United States Patent
Hsu et al.

(10) Patent No.: US 10,925,410 B2
(45) Date of Patent: Feb. 23, 2021

(54) MATTRESS WITH SENSOR MODULE FOR PATIENT CARE

(71) Applicant: MedicusTek, Inc., Taipei (TW)

(72) Inventors: Chia-Ming Hsu, Taipei (TW); Yi-Yuan Chen, Taipei (TW); Tsai-Yu Lin, Taipei (TW); Lavina Che-Hsuan Thong, Taipei (TW); Aaron R. Clousing, Costa Mesa, CA (US); Yu-Chun Hsu, Taipei (TW); Lee Lin, Taipei (TW)

(73) Assignee: MedicusTek, Inc., Taipei (TW)

( * ) Notice: Subject to any disclaimer, the term of this patent is extended or adjusted under 35 U.S.C. 154(b) by 382 days.

(21) Appl. No.: 15/881,421

(22) Filed: Jan. 26, 2018

(65) Prior Publication Data
US 2019/0231083 A1    Aug. 1, 2019

(51) Int. Cl.
A47C 27/08    (2006.01)
A47C 27/10    (2006.01)
A61G 7/057    (2006.01)
G16H 50/30    (2018.01)

(52) U.S. Cl.
CPC ............ A47C 27/083 (2013.01); A47C 27/10 (2013.01); A61G 7/05776 (2013.01); G16H 50/30 (2018.01)

(58) Field of Classification Search
CPC ............................ A47C 27/08; A47C 27/083
USPC ................................................. 5/710, 713
See application file for complete search history.

(56) References Cited

U.S. PATENT DOCUMENTS

| | | | |
|---|---|---|---|
| 2012/0079662 A1* | 4/2012 | Dzioba | A47C 27/083 5/713 |
| 2012/0116251 A1 | 5/2012 | Ben-Shalom et al. | |
| 2013/0191057 A1 | 7/2013 | Ben Shalom et al. | |
| 2014/0305445 A1 | 10/2014 | Morimura et al. | |
| 2014/0346836 A1 | 11/2014 | Briggs et al. | |
| 2016/0058641 A1 | 3/2016 | Moutafis et al. | |
| 2017/0086588 A1 | 3/2017 | Patrick et al. | |
| 2017/0312165 A1* | 11/2017 | Johnson | A61H 1/006 |

FOREIGN PATENT DOCUMENTS

| | | |
|---|---|---|
| CN | 206183513 U | 5/2017 |
| CN | 206612902 U | 11/2017 |
| WO | 2018032089 A1 | 2/2018 |

OTHER PUBLICATIONS

International Search Report issued in corresponding International Application No. PCT/US2019/012200 dated Apr. 1, 2019 (2 pages).

(Continued)

*Primary Examiner* — Fredrick C Conley
(74) *Attorney, Agent, or Firm* — Osha Bergman Watanabe & Burton LLP

(57) ABSTRACT

A mattress for patient care. The mattress includes a number of compressible cells and a number of sensors corresponding to the number of compressible cells. Each compressible cell is configured to contact, when inflated, a user in a contact area of a plurality of contact areas of the user. Each sensor is configured to generate a number of measurements, wherein each measurement relates to the contact area of a corresponding compressible cell. Each sensor is further configured to send the number of measurements to a pressure control device.

30 Claims, 13 Drawing Sheets

(56) References Cited

OTHER PUBLICATIONS

Written Opinion issued in corresponding International Application No. PCT/US2019/012200 dated Apr. 1, 2019 (11 pages).
Office Action issued in corresponding TW Application No. 108101954 dated Aug. 27, 2019 (18 pages).
Office Action issued in corresponding TW Application No. 108101954 dated Jan. 31, 2020 (18 pages).

* cited by examiner

MATTRESS WITH SENSOR MODULE FOR PATIENT CARE

BACKGROUND

Pressure ulcers (e.g., pressure sores, bedsores, or decubitus ulcers) often occur on skin overlying sacrum, coccyx, heels, hips, elbows, knees, back of shoulders, back of the cranium, etc. Pressure ulcers are localized damage to the skin and/or underlying tissue caused by pressure, or pressure in combination with shear and/or friction. Pressure ulcers may develop in individuals who are bedridden or confined to a wheelchair.

SUMMARY

In general, in one aspect, the invention relates to a mattress for patient care. The mattress includes a number of compressible cells each configured to contact, when inflated, a user in a contact area of a plurality of contact areas of the user, and a number of sensors corresponding to the number of compressible cells and configured to generate a number of measurements, wherein each measurement relates to the contact area of a corresponding compressible cell, and send the number of measurements to a pressure control device.

In general, in one aspect, the invention relates to a bed for patient care. The bed includes a plurality of compressible cells each configured to contact, when inflated, a user in a contact area of a plurality of contact areas of the user, a plurality of sensors corresponding to the plurality of compressible cells and configured to generate a plurality of measurements, wherein each of the plurality of measurements relates to the contact area of a corresponding compressible cell, and send the plurality of measurements to a pressure control device, and a bed frame configured to support the user lying on the plurality of compressible cells.

In general, in one aspect, the invention relates to a method for patient care. The method includes inflating, by a pressure control device, a plurality of compressible cells each contacting a user in a contact area of a plurality of contact areas of the user, and generating, by a plurality of sensors corresponding to the plurality of compressible cells, a plurality of measurements, wherein each of the plurality of measurements relates to the contact area of a corresponding compressible cell, wherein the plurality of sensors are coupled to form a sensor sheet, wherein the plurality of compressible cells are coupled to form a compressible cell sheet, wherein the sensor sheet and the compressible cell sheet are supported by a foam pad of the bed, and wherein the sensor sheet is attached to the compressible cell sheet to maintain a corresponding relationship between the plurality of compressible cells and the plurality of sensors.

Other aspects and advantages of the invention will be apparent from the following description and the appended claims.

DETAILED DESCRIPTION

Figure 1A:
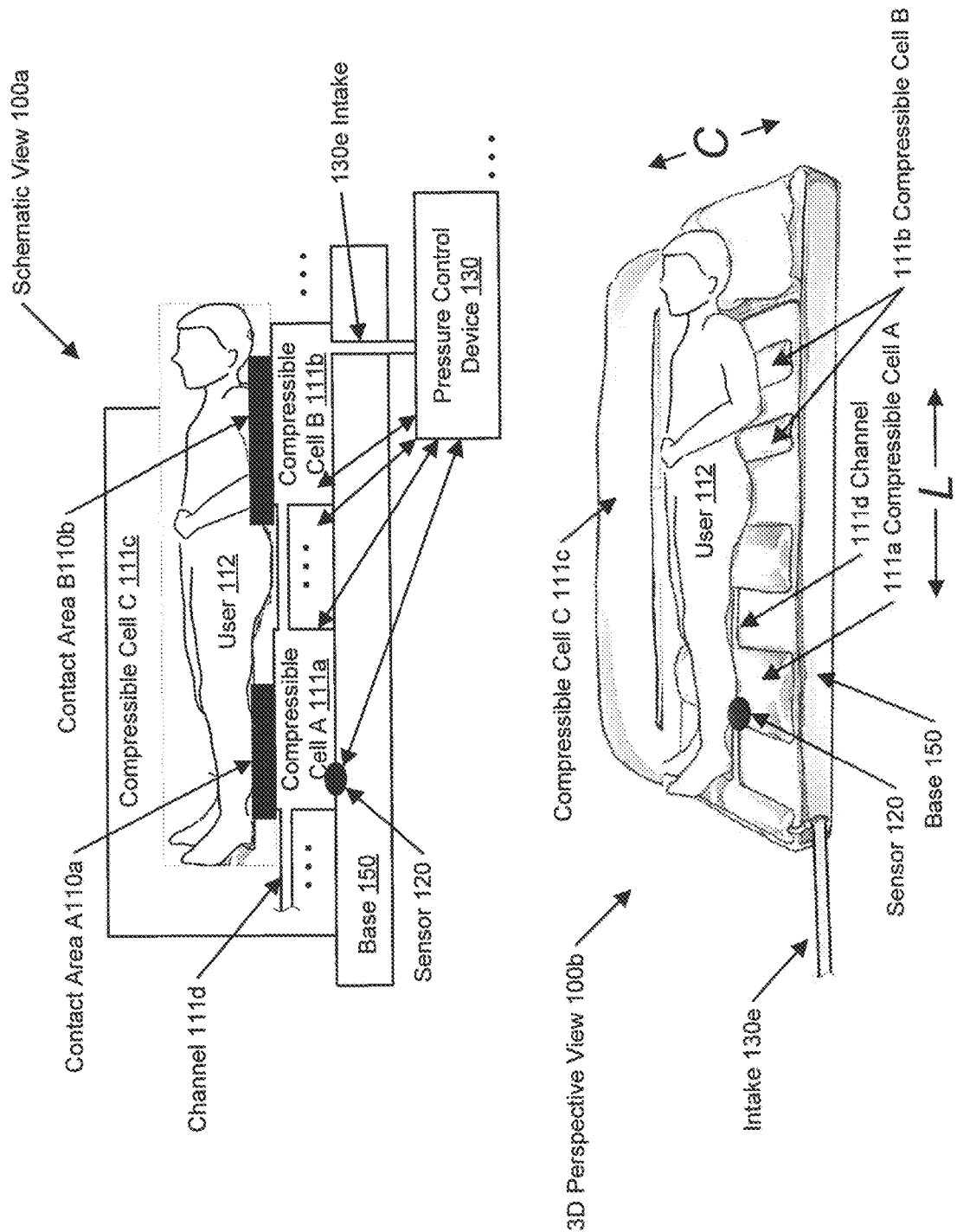
FIG. 1A shows a schematic diagram and a perspective view diagram of an air mattress with sensor module for patient care according to one or more embodiments of the invention.

Specific embodiments will now be described in detail with reference to the accompanying figures. Like elements in the various figures are denoted by like reference numerals for consistency. Like elements may not be labeled in all figures for the sake of simplicity.

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers does not imply or create a particular ordering of the elements nor limit any element to being only a single element unless expressly disclosed, such as by the use of the terms "before," "after," "single," and other such terminology. Rather, the use of ordinal numbers is to distinguish between the elements. By way of an example, a first element is distinct from a second element, and the first element may encompass more than one element and succeed (or precede) the second element in an ordering of elements.

It is to be understood that the singular forms "a," "an," and "the" include plural referents unless the context clearly dictates otherwise. Thus, for example, reference to "a horizontal beam" includes reference to one or more of such beams.

Terms like "approximately," "substantially," etc., mean that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

Although multiple dependent claims are not introduced, it would be apparent to one of ordinary skill in that that the subject matter of the dependent claims of one or more embodiments may be combined with other dependent claims. For example, even though claim 3 does not directly depend from claim 2, even if claim 2 were incorporated into independent claim 1, claim 3 is still able to be combined with independent claim 1 that would now recite the subject matter of dependent claim 2.

In general, embodiments of the invention relate to a mattress for patient care. The mattress includes a number of compressible cells and a number of sensors corresponding to the number of compressible cells. Each compressible cell is configured to contact, when inflated, a user in a contact area of a plurality of contact areas of the user. Each sensor is configured to generate a number of measurements, where each measurement relates to the contact area of a corresponding compressible cell. Each sensor is further configured to send the number of measurements to a pressure control device.

FIG. 1A shows a schematic diagram and a perspective view diagram of an air mattress with sensor module for patient care according to one or more embodiments of the invention. In one or more embodiments, one or more of the modules and elements shown in FIG. 1A may be omitted, repeated, and/or substituted. Accordingly, embodiments of an air mattress with sensor module for patient care should not be considered limited to the specific arrangements of modules shown in FIG. 1A.

Specifically, FIG. 1A shows a schematic view (100a) and an example 3-dimensional (3D) perspective view (100b) of the air mattress with sensor module for patient care used by a user (112). In particular, in the 3D perspective view (100b), the longitudinal direction of the user (112) is denoted as "L" while the sideways direction of the user (112) is denoted as "C". In one or more embodiments of the invention, the air mattress with sensor module for patient care depicted in FIG. 1A may be included in a bed, a wheel chair, or other device for supporting the user (112) in a pre-determined posture, such as lying, sitting, standing, leaning, etc. postures. The air mattress with sensor module for patient care includes multiple compressible cells (e.g., compressible cell A (111a), compressible cell B (111b), compressible cell C (111c)) disposed on a base (150) and coupled to a pressure control device (130). The base (150) is a structural element that supports the multiple compressible cells (e.g., compressible cell A (111a), compressible cell B (111b), compressible cell C (111c)) against the user (112) in the pre-determined posture. For example, the base (150) may be constructed using memory foam of a particular density. As used herein, memory foam refers to viscoelastic polyurethane foam or low-resilience polyurethane foam (LRPu) that softens in reaction to body heat and conforms to a body contour within a few minutes. In another example, the base (150) may be a film or a sheet of suitable material (e.g., vinyl, plastic, cloth, etc. or other material used to construct the compressible cells) that connects the multiple compressible cells (e.g., compressible cell A (111a), compressible cell B (111b), compressible cell C (111c)) into a single item.

In one or more embodiments of the invention, the user (112) is a patient, such as a human patient or an animal patient. In one or more embodiments, the compressible cell is a flexible enclosure configured to contain a volume of compressible fluid, such as air, a mixture/combination of air or other gas with liquid (e.g., water), a jell that contains air or other gas pocket(s)/bubble(s), etc. For example, the flexible enclosure may be constructed using flexible material, such as rubber, vinyl, thermoplastic polyurethane (TPU), polyvinyl chloride (PVC), latex, textile reinforced urethane, and have any shape or size. In particular, the flexible enclosure may be constructed using a film of such flexible material.

In one or more embodiments, the compressible cells (e.g., compressible cell A (111a), compressible cell B (111b), compressible cell C (111c)) are inflated and/or deflated via an intake (130e) (e.g., a valve, hose, tube, pipe, etc.) to maintain and/or adjust a fluid pressure. Throughout this disclosure, the term "inflate" refers to the act of supplying fluid to increase pressure while the term "deflate" refers to the act of releasing fluid to decrease pressure. For example, the compressible cells may include an air cell that is inflated and/or deflated using air to maintain and/or adjust an air pressure. In one or more embodiments, one or more of the compressible cells (e.g., compressible cell A (111a)) are inflated and/or deflated by a pressure control device (130). In one or more embodiments, one or more of the compressible cells (e.g., compressible cell B (111b)) are inflated and/or deflated by the pressure control device (130) via intervening compressible cells (e.g., compressible cell A (111a)) and connecting fluid channels (e.g., channel (111d)). The fluid channel is a fluid passage connecting two or more compressible cells. In one or more embodiments, the fluid channel has a substantially smaller (e.g., by a factor of 4 or more) cross-sectional area than the connected compression cells such that the connected compression cells maintain respective shapes/sizes substantially independent of each other. In one or more embodiments, all compression cells (e.g., compressible cell A (111a), compressible cell B (111b), compressible cell C (111c)) are connected together using intervening fluid channels and receive fluids from a single pressure control device (i.e., pressure control device (130)). In one or more embodiments, the compression cells (e.g., compressible cell A (111a), compressible cell B (111b), compressible cell C (111c)) are divided into multiple compression cell groups. The compression cell group is a group of compression cells that are connected together using intervening fluid channels and receive fluids from a single pressure control device (e.g., pressure control device (130)). In other words, the air mattress with sensor module for patient care depicted in FIG. 1A may include multiple pressure control devices (e.g., pressure control device (130)) each used to inflate and/or deflate one compression cell group.

In one or more embodiments, the pressure control device (130) may include a pump, for example an air pump. The fluid pressure (e.g., air pressure) may be maintained and/or adjusted statically to remain a constant level, or maintained/adjusted dynamically to have varying levels with respect to time. In one or more embodiments, the pressure control device (130) may adjust the fluid pressures of multiple compression cell groups in a pre-determined sequence. For example, the pressure control device (130) may inflate (i.e., supply additional fluid to increase the fluid pressure) a first compression cell group while deflate (i.e., release fluid to decrease the fluid pressure) a second compression cell group during a first adjustment time period. In this context, the first adjustment time period is an inflation time period for the first compression cell group and is a deflation time period for the second compression cell group. Subsequently, the pressure control device (130) may deflate the first compression cell group while inflate the second compression cell group during a second adjustment time period. In this context, the second adjustment time period is a deflation time period for the first compression cell group and is an inflation time period for the second compression cell group. The first adjustment time period and the second adjustment time period may be recurring time periods that alternate between each other. In one or more embodiments, the first adjustment time period and the second adjustment time period are separated by an inactive time period during which the first compression cell group and he second compression cell group are not being inflated or deflated. For example, the pump may be turned off or otherwise inactive during the inactive time period. In one or more embodiments, the inflation time period of the first compressible cell group and the deflation time period of the second compressible cell group do not overlap each other and are separated by an inactive time period. In one or more embodiments, the deflation time period of the first compressible cell group and the inflation time period of the second compressible cell group do not overlap each other and are separated by an inactive time period. In one or more embodiments, each compressible cell group is inflated and deflated using the method described in reference to FIG. 5B below.

In one or more embodiments, the enclosure of the air cell includes one or more pin holes such that the air pressure is maintained and/or adjusted with air constantly flowing in from the intake then exiting through the pin hole(s). This air flow may affect temperature and humidity in the vicinity of the user (112). In particular, the air flow may alter the microclimate near the user's skin in a manner that reduces the risk of pressure ulcers.

In one or more embodiments, by way of the pressure control device (130), the compressible cell (e.g., compressible cell A (111a), compressible cell B (111b)) is configured to inflate based at least on a characteristic of a contact area (e.g., contact area A (110a), contact area B (110b)) of the user (112). In response to inflating, the compressible cell A (111a) and compressible cell B (111b) contacts the user (112) in the contact area A (110a) (e.g., lower leg area) and contact area B (110b) (e.g., shoulder blade area), respectively. Once inflated, the compressible cell exhibits an inflated contour based on a pre-inflation contour and the characteristic of the contact area. As used herein, the inflated contour is an outline or other type of shape of the compressible cell subsequent to being inflated. In contrast, the pre-inflation contour is an outline or other type of shape of the compressible cell prior to being inflated. In one or more embodiments, the characteristic of the contact area includes a body contour area and/or an underlying body composition of the user (112) in the contact of the user (112). For example, the inflated contour of the compressible cell A (111a) substantially conforms to the body contour of the lower leg of the user (112) to the extent bounded by the pre-inflation contour of the compressible cell A (111a). Similarly, the inflated contour of the compressible cell B (111b) substantially conforms to the body contour of the shoulder of the user (112) to the extent bounded by the pre-inflation contour of the compressible cell B (111b).

At the contact area A (110a), the weight and compliableness (i.e., soft or hard) of the lower leg portion of the user (112), the fluid pressure and compliableness of the compressible cell A (111a), and a force (e.g., tension) in the flexible enclosure of the compressible cell A (111a) interact with each other to reach a balance of forces. Similarly, at the contact area B (110b), the weight and compliableness of the shoulder blade portion of the user (112), the fluid pressure and compliableness of the compressible cell B (111b), and the force (e.g., tension) in the flexible enclosure of the compressible cell B (111b) interact with each other to reach another balance of forces. Due to different body compositions of the user (112) at the lower leg (i.e., dominated by flesh) versus the shoulder blade (i.e., dominated by bone), the balance of forces at the contact area A (110a) differs from the balance of forces at the contact area B (110b) to result in different pressures applied to and received by the user (112) at the contact area A (110a) and the contact area B (110b). The pressure applied to and received by the user (112) at a particular contact area is referred to as the skin pressure at the contact area. To further enlarge the difference in skin pressures applied to and received by the user (112), the balance of forces at the contact area A (110a) may further differ from the balance of forces at the contact area B (110b) due to different body contours of the lower leg versus shoulder blade, as well as different pre-inflation contours of the compressible cell A (111a) versus compressible cell B (111b). Furthermore, the skin pressures may also depend on the overall body weight of the user (112).

In one or more embodiments, one or more pressure sensors are disposed on one or more compressible cells (e.g., the sensor (120) on the compressible cell A (111a)). For example, the pressure sensor (e.g., the sensor (120)) may be disposed at the interface between the compressible cell (e.g., compressible cell A (111a)) and the base (150). In another example, the pressure sensor (e.g., the sensor (120)) may be disposed at the interface between the user (112) and the compressible cell (e.g., compressible cell A (111a)). In yet another example, the pressure sensor (e.g., the sensor (120)) may be disposed in a bed sheet, duvet cover, comforter, quilt, or other bedding items. In one or more embodiments, the sensor (120) is configured to generate a pressure measurement representing the interface pressure exerted at the corresponding interface. In one or more embodiments, the sensor (120) is further configured to send a signal (representing the pressure measurement) to the pressure control device (130) to facilitate adjusting the air pressure of the compressible cell A (111a) based at least on the pressure measurement. For example, the signal may be displayed by the pressure control device (130) to a healthcare professional. In another example, the signal may trigger an automatic action of the pressure control device (130). In one or more embodiments, the sensor (120) may also include a temperature sensor or humidity sensor.

In one or more embodiments, if the pressure measurement exceeds a pre-determined high threshold indicating skin ulcer risk (referred to the pressure ulcer risk index), the pressure control device (130) releases, manually controlled or automatically triggered, certain amount of fluid (e.g., air) from the compressible cell A (111a), via intervening compressible cell(s) and fluid channel(s)), to reduce the interface pressure, and therefore reducing the corresponding skin pressure for mitigating the skin ulcer risk.

In one or more embodiments, if the pressure measurement exceeds another pre-determined high threshold indicating over-compression of the compressible cell A (111a) (referred to the bottom out condition), the pressure control device (130) injects, manually controlled or automatically triggered, certain amount of fluid (e.g., air) into the compressible cell A (111a), via intervening compressible cell(s) and fluid channel(s)), to correct the bottom out condition. For example, the bottom out condition may occur when the user (112) is sitting over the compressible cell A (111a) causing the fluid to be pushed out of the compressible cell A (111a). In another example, the bottom out condition may occur when the user (112) has excessively high body weight causing the fluid in the compressible cell A (111a) to be pushed out. In yet another example, the bottom out condition may occur during a deflation cycle if too much fluid (e.g., air) is released considering the user's body weight and/or posture induced body weight concentration. In the bottom out condition, the top surface and the bottom surface of the compressible cell A (111a) may eventually come into contact with each other at one or more locations within the compressible cell A (111*a*) and cause permanent deformation of the compressible cell A (111*a*).

In one or more embodiments, if the pressure measurement is less than a pre-determined low threshold indicating lack of body support, the pressure control device (130) injects, manually controlled or automatically triggered, certain amount of fluid (e.g., air) into the compressible cell A (111*a*), via intervening compressible cell(s) and fluid channel(s)), to increase the interface pressure for improving the support of the posture of the user (112).

In one or more embodiments, the compressible cell C (111*c*) has an inflated height that is higher than the compressible cell A (111*a*) and compressible cell B (111*b*). The air pressure of the compressible cell C (111*c*) serves to impede a lateral movement of the user (112) to prevent the user (112) from leaving or accidentally rolling or falling off the compressible cells and/or the base (150). Although the user (112) is shown in FIG. 1A as lying on the compressible cells (e.g., compressible cell A (111*a*), compressible cell B (111*b*), compressible cell C (111*c*)), as noted above, the user (112) may also assume other postures (e.g., sitting, standing, leaning, etc.) with respect to the compressible cells.

In one or more embodiments, the compressible cells (e.g., compressible cell A (111*a*), compressible cell B (111*b*), compressible cell C (111*c*)) are inflated and deflated using the method described in reference to FIG. 5A below.

Figure 1B:
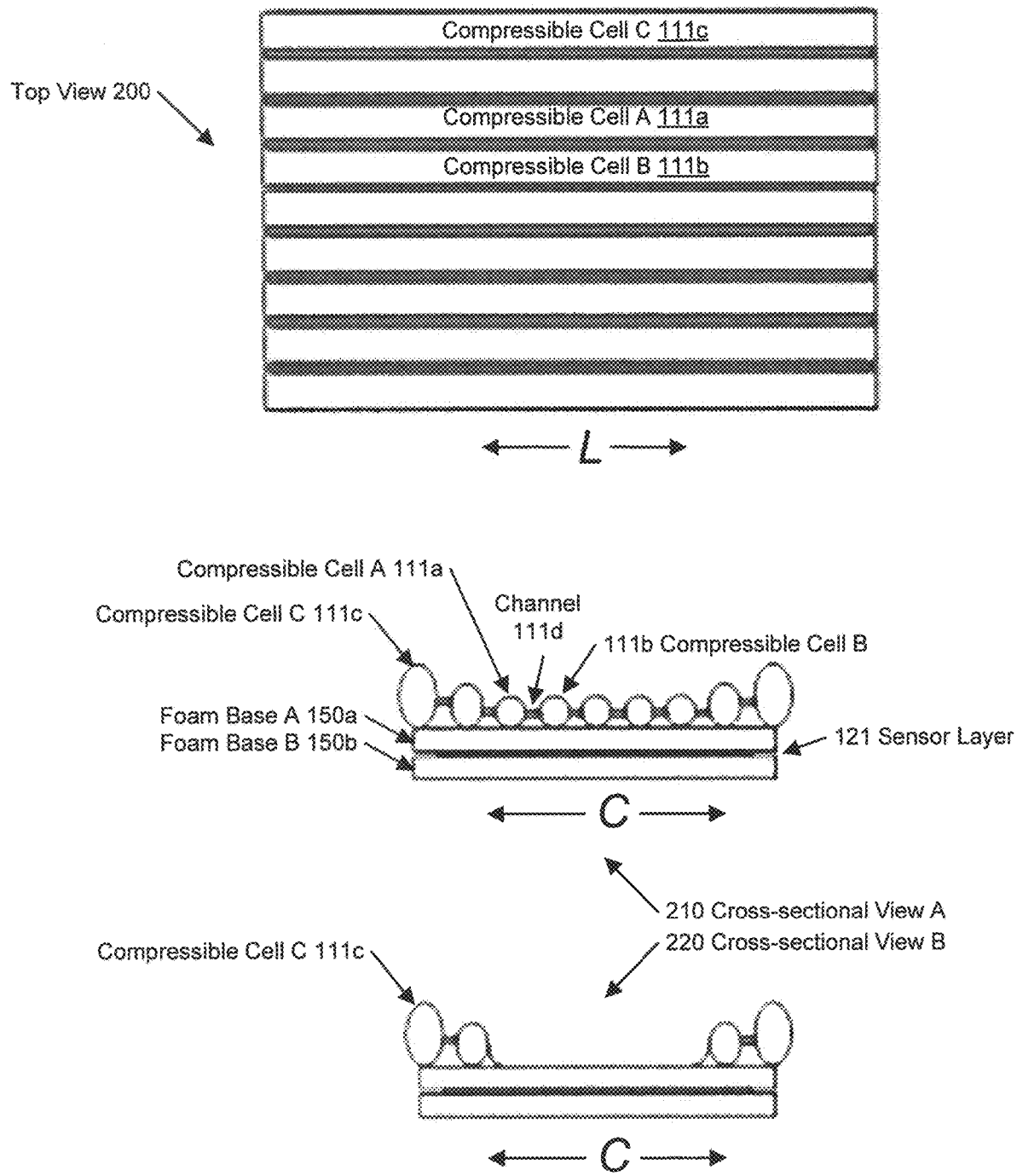
FIG. 1B shows a top view diagram and a cross-sectional view diagram of an air mattress with sensor module for patient care according to one or more embodiments of the invention.

FIG. 1B shows a top view diagram and a cross-sectional view diagram according to one or more embodiments of the invention. In one or more embodiments, one or more of the modules and elements shown in FIG. 1B may be omitted, repeated, and/or substituted. Accordingly, embodiments of an air mattress with sensor module for patient care should not be considered limited to the specific arrangements of modules shown in FIG. 1B.

Specifically, FIG. 1B shows a top view (200) and corresponding cross-sectional view A (210) and cross-sectional view B (220) of an example user posture support device. The example user support device depicted in FIG. 1B has a different layout than the user support device depicted in the 3D perspective view (100*b*) depicted in FIG. 1A above. Specifically, the top view (200) shows compressible cells (e.g., compressible cell A (111*a*), compressible cell B (111*b*), compressible cell C (111*c*)) as parallel rectangles along the longitudinal direction "L" of a user (not shown) that, e.g., may correspond to the user (112) depicted in FIG. 1A above. Correspondingly, the cross-sectional view A (210) shows a cross-section of the parallel compressible cells depicted in the top view (200). Each of the parallel rectangular shaped compressible cells (e.g., compressible cell A (111*a*), compressible cell B (111*b*), compressible cell C (111*c*)) is depicted as an oval shaped cross-section along the sideways direction "C" in the cross-sectional view A (210). In one or more embodiments, adjacent parallel rectangular shaped compressible cells (e.g., compressible cell A (111*a*), compressible cell B (111*b*)) are connected via fluid channels (e.g., channel (111*d*)). In one or more embodiments, odd numbered parallel rectangular shaped compressible cells (e.g., compressible cell A (111*a*), compressible cell C (111*c*)) are connected via fluid channels (not shown) into a first compressible cell group while even numbered parallel rectangular shaped compressible cells (e.g., compressible cell B (111*b*)) are connected via fluid channels (not shown) into a second compressible cell group. As described in reference to FIG. 1A above, the first compressible cell group and the second compressible cell group may be inflated/deflated in a pre-determined alternating time sequence to reduce skin pressure concentration to a particular region of the body of the user (112). In one or more embodiments, inflating/deflating compressible cell group(s) in a pre-determined alternating time sequence is performed using the method described in reference to FIG. 5B below.

The base (150) depicted in FIG. 1B above is shown as two layers (i.e., foam base A (150*a*) and foam based B (150*b*), e.g., constructed using memory foam) overlapping each other where the sensor layer (121) is disposed in-between the foam base A (150*a*) and the foam based B (150*b*). For example, the sensor layer (121) may include multiple pressure sensors, such as the sensor (120) depicted in FIG. 1A above.

The cross-sectional view B (220) shows a variation of the cross-sectional view A (210) where five parallel rectangular shaped compressible cells are omitted from the example depicted in the top view (200) and corresponding cross-sectional view A (210).

Figure 2A:
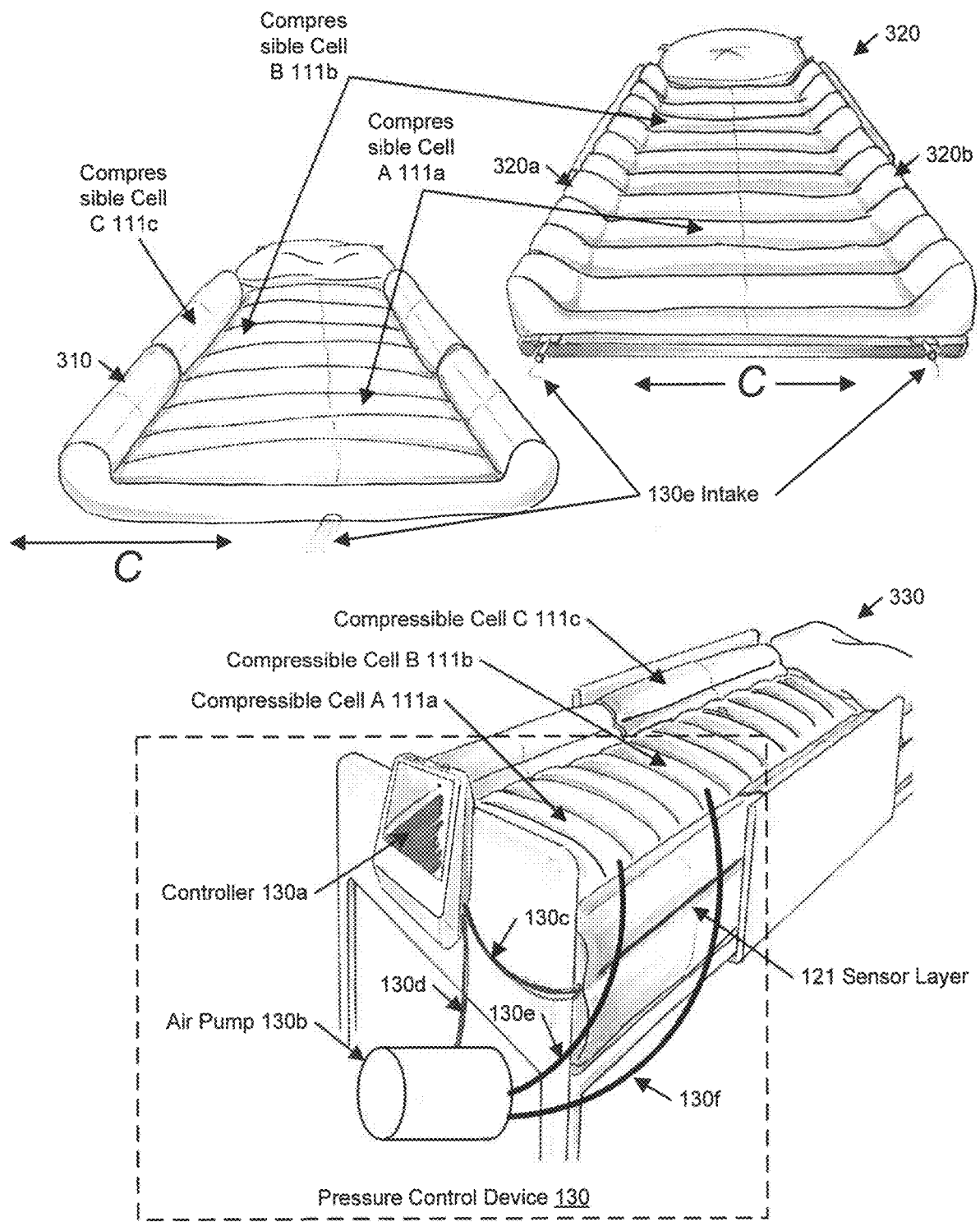
FIGS. 2A and 2B show example air mattress with sensor module for patient care according to one or more embodiments of the invention.
Figure 2B:
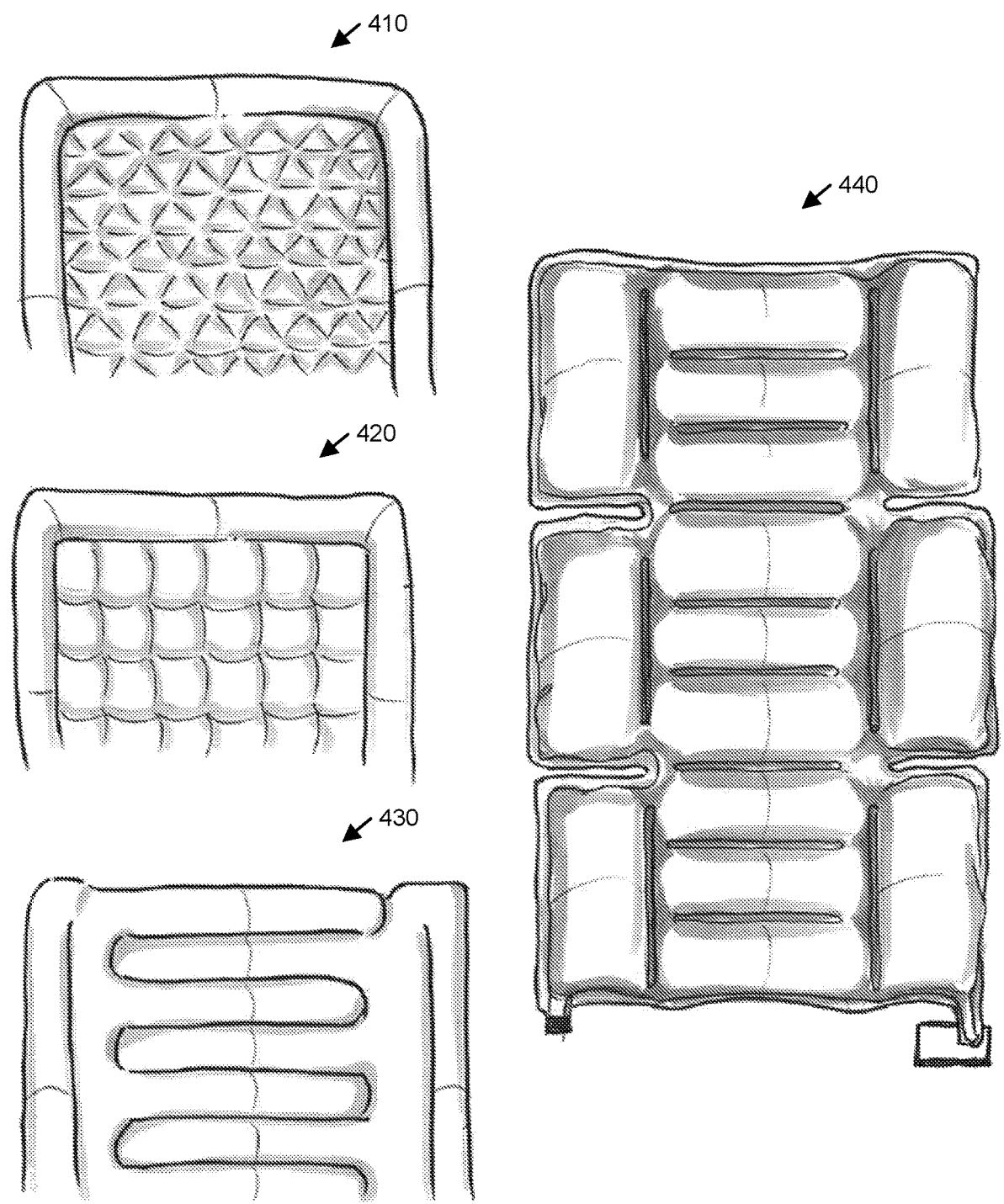

FIGS. 2A and 2B show examples of an air mattress with sensor module for patient care according to one or more embodiments of the invention. In one or more embodiments, one or more of the modules and elements shown in FIGS. 2A and 2B may be omitted, repeated, and/or substituted. Accordingly, embodiments of the air mattress with sensor module for patient care should not be considered limited to the specific arrangements of modules shown in FIGS. 2A and 2B.

Specifically in FIG. 2A, the example (310) shows inflated compressible cells (e.g., compressible cell A (111*a*), compressible cell B (111*b*)) that are parallel to each other along the sideways direction "C". Additional inflated compressible cells (e.g., compressible cell C (111*c*)) with elevated heights are added along the perimeter of the parallel compressible cells to prevent the user from leaving or accidentally rolling or falling off the air mattress with sensor module for patient care.

In addition, the example (320) shows a variation to the example (310) where each of the inflated compressible cells (e.g., compressible cell A (111*a*), compressible cell B (111*b*)) has raised ends (e.g., end A (320*a*), end B (320*b*)) to prevent the user from leaving or accidentally rolling or falling off the air mattress with sensor module for patient care.

The example (330) shows the air mattress with sensor module for patient care configured as a bed having a mattress depicted in the example (310). In particular, the bed includes a pressure control device (130) having a controller (130*a*) and an air pump (130*b*). In one or more embodiments, the controller (130*a*) may be part of a computing system described in reference to FIGS. 8A and 8B below. For example, the controller (130*a*) may exchange data and other information with a cloud based computing resource depicted in FIGS. 8A and 8B below.

In one or more embodiments, the air pump (130*b*) is used to inflate and/or deflate the compressible cells (e.g., compressible cell A (111*a*), compressible cell B (111*b*), compressible cell C (111*c*)) via one or more intakes (e.g., intake (130*e*), intake (1300). By having separate and independent intakes (e.g., intake (130*e*), intake (1300, the air pressures of the compressible cell A (111*a*) and compressible cell B (111*b*) are separately and independently adjustable using separate air outputs of the air pump (130*b*). This allows different body portions (e.g., lower leg, shoulder blades) of the user to experience different skin pressures. In one or more embodiments, the compressible cell A (111*a*) and compressible cell B (111*b*) belong to separate compressible cell groups and are separately and independently adjustable using the separate and independent intakes (e.g., intake (130e), intake (1300).

The sensor layer (121) generates pressure measurements for sending via a signal cable (130c) to the controller (130a) that controls the air pump (130b) via a controlling cable (130d). According to the displayed pressure readings, reflecting the skin pressures applied to and received by different body portions (e.g., lower leg, shoulder blades) of the user, a healthcare professional may adjust the pressure outputs of the air pump (130b) to lower the air pressure of one or more of the compressible cell(s) to reduce corresponding skin pressure(s) and ulcer risk(s). In another example, the healthcare professional may adjust the pressure outputs of the air pump (130b) to raise the air pressure to improve support to the user's posture. In yet another example, the pressure measurements may be analyzed to detect an excessive pressure ulcer risk index, a bottom out condition, a change in user posture (e.g., from the lying posture to the sitting posture), an intentional or accidental user movement away from the bed, or other pre-determined condition. Each of these detected conditions (referred to as notable condition) may generate a specific alert to the healthcare professional for taking appropriate patient care actions. In one or more embodiments, the pressure measurements are analyzed by the controller (130a) to detect these conditions and generate corresponding alerts. In one or more embodiments, the pressure measurements are transmitted by the controller (130a) to a cloud based computing resource that in turn detects these conditions and generates corresponding alerts. For example, the cloud based computing resource may transmit the alerts to a healthcare professional who is remote from the bed and user depicted in the example (330). An example of the controller (130a) interacting with the cloud based computing resource is described in reference to FIGS. 8A and 8B below. An example of the controller (130a) and/or the cloud based computing resource analyzing the pressure measurements to detect notable conditions is described in reference to FIGS. 6 and 7 below.

In addition to the various layout patterns for compressible cells shown and described in reference to FIG. 2A above, FIG. 2B shows additional example layouts (410-440) of the compressible cells for the air mattress with sensor module for patient care. Although specific shapes of the compressible cells are shown in FIGS. 2A and 2B, other shapes may also be used without deviating from the invention.

TABLE 1 shows example parameters of the compressible cells and associated components of the air mattress with sensor module for patient care depicted in FIGS. 1A-2B above. The height range refers to the vertical dimension perpendicular to the aforementioned longitudinal direction "L" and the sideways direction "C". The width range refers to the shorter of the other two dimensions along either the longitudinal direction "L" or the sideways direction "C".

TABLE 1

|  | Height Range | Width Range |
| --- | --- | --- |
| Compressible Cell A or B | 0.4~20 cm | 9.5~40 cm |
| Compressible Cell C | 0~40 cm | 0~15 cm |
| Channel | N/A | 0~20 cm |
| Foam Base A | 0~20 cm | >30 cm |
| Foam Base B | 0~20 cm | >30 cm |

Figure 3A:
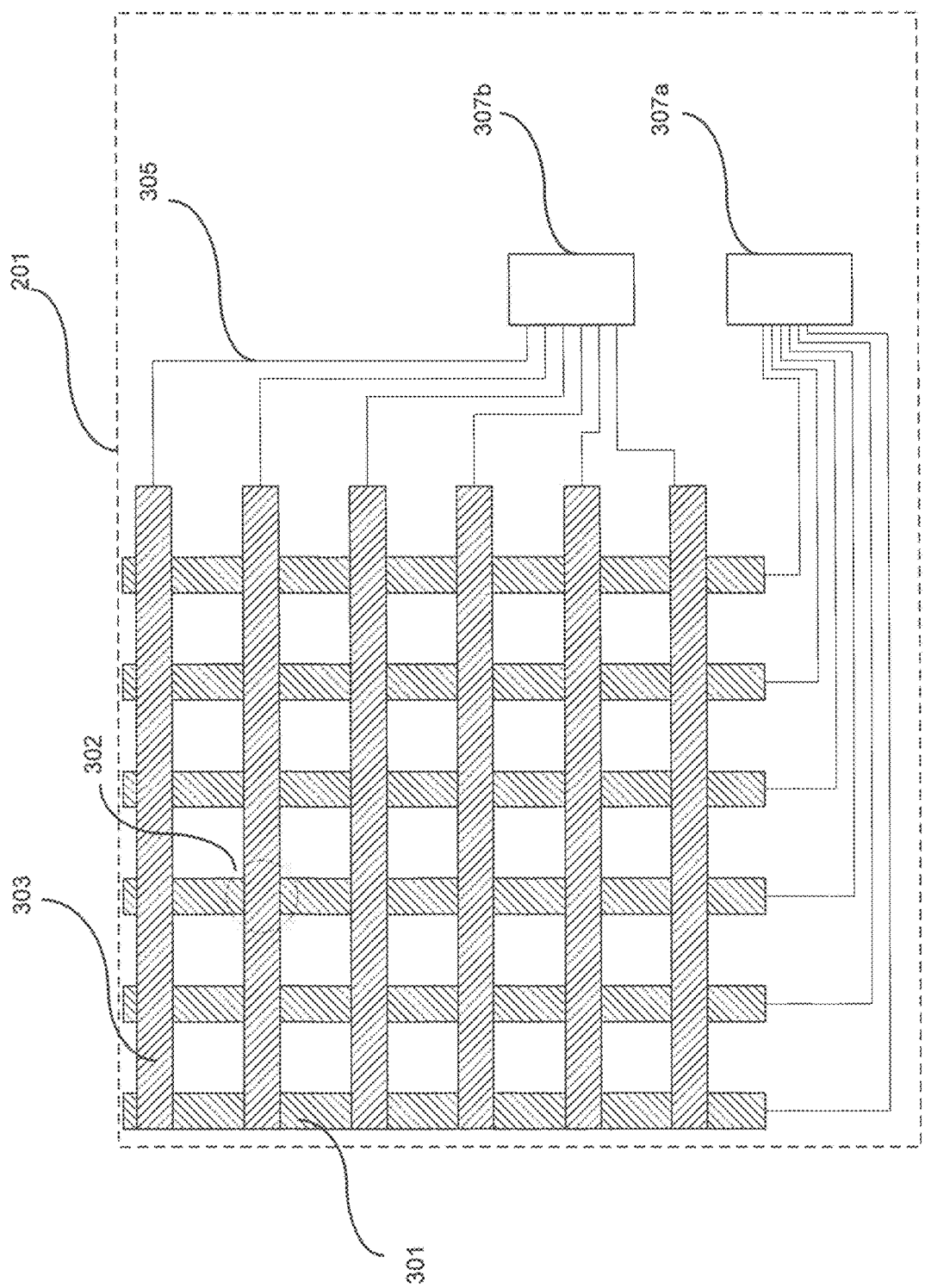
FIG. 3A shows example details of a sensor module according to one or more embodiments of the invention.

FIG. 3A shows example details of a sensor module (201) according to one or more embodiments of the invention. In one or more embodiments, the sensor (120) depicted in FIG. 1A above is included in the sensor module (201). In one or more embodiments, the sensor module (201) corresponds to the sensor layer (121) depicted in FIGS. 1B and 2A above. In one or more embodiments, one or more of the modules and elements shown in FIG. 3A may be omitted, repeated, and/or substituted. Accordingly, embodiments of the air mattress with sensor module for patient care should not be considered limited to the specific arrangements of modules shown in FIG. 3A.

As shown in FIG. 3A, the sensor module (201) includes a first layer electrode (301), a second layer electrode (303), wires (305), and connectors (307a-b). The various components and structures of the sensor module (201) listed above may interact directly or indirectly with one another. Each of these components will be described below in more detail.

In one or more embodiments, the first layer electrode (301) may be a conducting electrode in the shape of a rectangle. In one or more embodiments, the sensor module (201) may include more than one first layer electrode (301). In the case where the sensor module (201) includes more than one first layer electrodes (301), multiple first layer electrodes (301) are disposed in parallel to each other forming a 2D plane, and are highlighted in FIG. 3A using the same hatch pattern. In one or more embodiments, multiple first layer electrodes (301) are constructed from depositing electrically conducting material onto a substrate to form the pattern of parallel rectangles shown in FIG. 3A. As used herein, electrically conducting material is a material that allows the flow of electrical current in one or more directions.

In one or more embodiments, the particular shape and size of the first layer electrode (301), the number of first layer electrodes (301) in the sensor module (201), and the distance between each of the multiple first layer electrodes (301) may vary, based on the particular application of the sensor module (201), without departing from the scope of the invention. For example, the first layer electrode (301) may have a circular, elliptical, or other curvilinear shape.

In one or more embodiments, the second layer electrode (303) may be a conducting electrode in the shape of a rectangle. In one or more embodiments, the sensor module (201) may include more than one second layer electrode (303). In the case where the sensor module (201) includes more than one second layer electrodes (303), multiple second layer electrodes (303) are disposed in parallel to each other forming a 2D plane, and are highlighted in FIG. 3A using the same hatch pattern. In one or more embodiments, the multiple second layer electrodes (303) are constructed from depositing electrically conducting material onto a substrate to form the pattern of parallel rectangles shown in FIG. 3A.

In one or more embodiments, the particular shape and size of the second layer electrode (303), the number of second layer electrodes (303) in the sensor module (201), and the distance between each of the plurality of second layer electrodes (303) may vary, based on the particular application of the sensor module (201), without departing from the scope of the invention. For example, the second layer electrode (303) may have a circular, elliptical, or other curvilinear shape.

In one or more embodiments, the first layer electrode (301) and the second layer electrode (303) are disposed to be perpendicular with each other and overlapping each other in the 2D plane. As shown in FIG. 3A, the first layer electrode (301) is obscured by the second layer electrode (303) in each overlapping region (e.g., overlapping region (302)). In one or more embodiments, the first layer electrode (301) and the second layer electrode (303) may form any angle other than being perpendicular with each other. The first layer electrode (301) and the second layer electrode (303) may have, but is not limited to, the same material composition.

In one or more embodiments, the wires (305) may be electrical wires made of copper (e.g., etched copper pattern in a flexible printed circuit board (flex-PCB) construction) or silver (e.g., silver paste screen-printed onto a laminated polymer film). The wires (305) may be insulated with a plastic material, such as polyethylene terephthalate (PET), thermoplastic polyurethane (TPU), polyimide (PI), etc. The wires (305) may be wires of a ribbon connector with one end of the ribbon connector including one of the connectors (307a-b) and the other end with trimmed and exposed wires (305).

The connectors (307a-b) may be connector heads of a ribbon connector. The connectors (307a-b) may be male or female connector heads. One of the connectors (307a-b) is an input connector and the other of the connectors (307a-b) is an output connector. The connectors (307a-b) are configured to be connected to the I/O circuits of the computing device.

In one or more embodiments, although FIG. 3A only shows two connectors (307a-b), the sensor module (201) may have more than two connectors (307a-b) without departing from the scope of the invention.

Figure 3B:
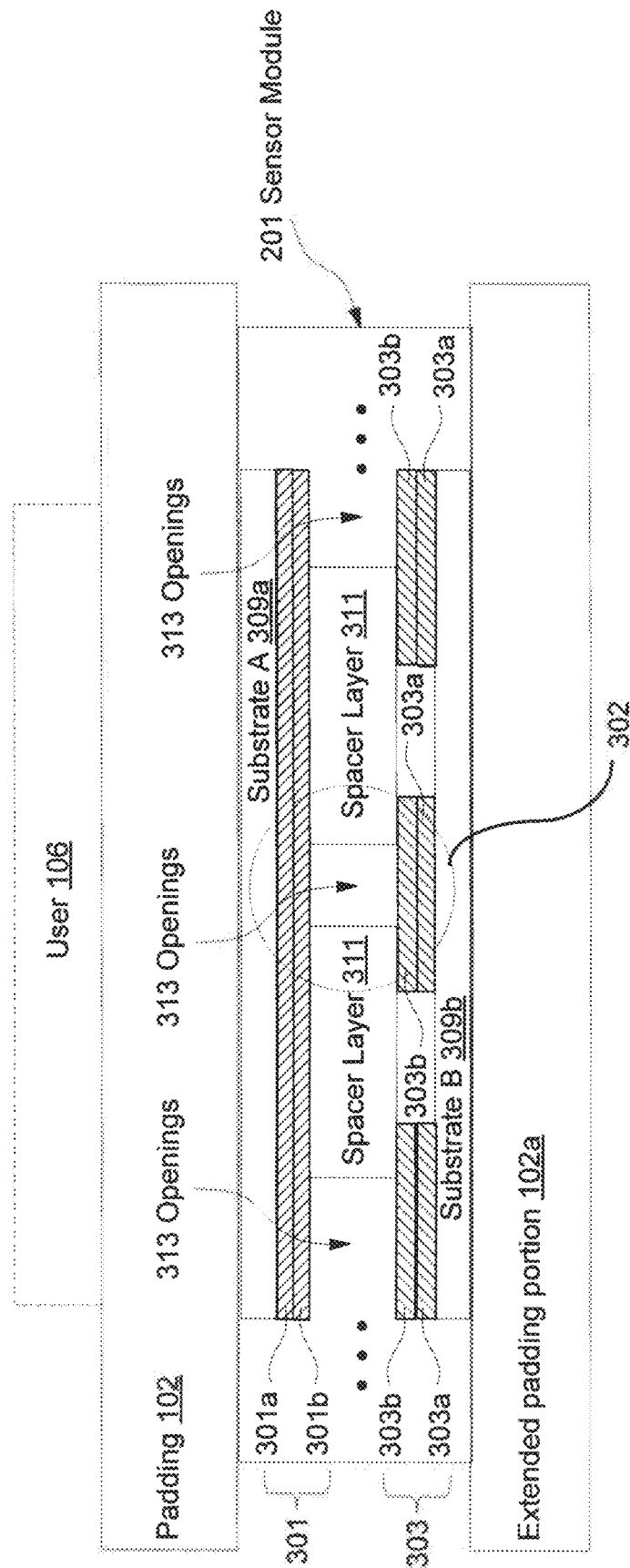
FIG. 3B shows an example cross-sectional view of the sensor module according to one or more embodiments of the invention.

As shown in FIG. 3A, in one or more embodiments, the wires (305) electrically connect the connector (307a) with the first layer electrode (301) and the connector (307b) with the second layer electrode (303). One of ordinary skill would appreciate that the connection scheme between the electrode layers and the connectors (307a-b) may vary without departing from the scope of the invention FIG. 3B shows an example cross-sectional view of the sensor module (201) according to one or more embodiments of the invention. In one or more embodiments, FIG. 3B shows an example cross-sectional view of the sensor layer (121) depicted in FIGS. 1B and 2A above. In one or more embodiments, one or more of the modules and elements shown in FIG. 3B may be omitted, repeated, and/or substituted. Accordingly, embodiments of the air mattress with sensor module for patient care should not be considered limited to the specific arrangements of modules shown in FIG. 3B.

As shown in FIG. 3B, a user (106) (e.g., a patient, such as a human patient or an animal patient) may be lying down on, sitting on, or stepping on the sensor module (201). As shown in the cross-sectional view, the sensor module (201) is disposed in-between a padding (102) and extended padding portion (102a), which may correspond to the foam base A (150a) and foam base B (150b) depicted in FIG. 1B above. Specifically, the sensor module (201) includes a substrate A (309a), a substrate B (309b), a spacer layer (311), and openings (313). The various components and structures of the sensor module (201) listed above may interact directly or indirectly with one another. Each of these components will be described below in more detail.

In one or more embodiments of the invention, the substrate A (309a) and the substrate B (309b) include flexible films, the materials of which may be one independently selected from the group consisting of: polyethylene terephthalate (PET), thermoplastic polyurethane (TPU), polyimide (PI), other plastics, other flexible materials, and combinations thereof. In one or more embodiments, the substrate A (309a) and/or the substrate B (309b) may be supplemented with a padding (102) of cloth or some other soft material, such as cotton, flax wool, ramie, silk, leather and fur etc. that can minimize or reduce noise as well as enhance comfort level when the user (106) interacts with the substrate A (309a) and/or the substrate B (309b).

In one or more embodiments of the invention, the thickness of the substrate A (309a) and the substrate B (309b) may be, but is not limited to, 0.0014 millimeter (mm) or more. In an example construction (referred to as construction A), the padding (102) may have a nominal thickness 2 centimeter (cm) separating the user (106) from the sensor module (201), and the substrate A (309a) and/or the substrate B (309b) may include a PET film having nominal thickness 0.025 mm laminated with a PI film having nominal thickness 0.025 mm. In another example construction (referred to as construction B), the padding (102) may have a nominal thickness grater than 5 cm separating the user (106) from the sensor module (201), and the substrate A (309a) and/or the substrate B (309b) may include a PET film having nominal thickness 0.188 mm laminated with a PI film having nominal thickness 0.025 mm. Although the padding (102) is shown to be disposed between the user (106) and the sensor module (201), in one or more embodiments, the padding (102) may extend to include an extended padding portion (102a) to enclose at least a portion of the sensor module (201). For example, while the as-shown portion of the padding (102) may be disposed between the user (106) and the sensor module (201), the extended padding portion (102a) of the padding (102) may be disposed on a different side of the sensor module (201) that is not in contact with the user (106). Further, the padding (102) and substrate A (309a) may be integrated or otherwise combined into a single item. Similarly, the padding (102a) and substrate B (309b) may be integrated or otherwise combined.

In one or more embodiments of the invention, the spacer layer (311) is a flexible and deformable insulating material, which may be one selected from the group consisting of polyethylene terephthalate (PET), thermoplastic polyurethane (TPU), polyimide (PI), synthetic or natural sponge, foamed plastics, and combinations thereof. In one or more embodiments of the invention, the thickness of the spacer layer (311) may be, but is not limited to, 3 mm or more. In the example construction A, the spacer layer (311) may include a TPU film with nominal thickness 0.02 mm. In the example construction B, the spacer layer (311) may include a TPU film with nominal thickness between 0.2 mm and 0.5 mm.

As shown in FIG. 3B, the first layer electrode (301) includes multiple laminated layers (e.g., layer (301a), layer (301b)) and is disposed on the substrate A (309a). Similarly, the second layer electrode (303) includes multiple laminated layers (e.g., layer (303a), layer (303b)) and is disposed on the substrate B (309b). In one or more embodiments, the first layer electrode may be disposed on the substrate B (309b) and the second layer electrode may be disposed on the substrate A (309a). In one or more embodiments, the layer (301a) and/or layer (303a) are constructed using copper (e.g., etched copper pattern in a flex-PCB construction) or silver (e.g., silver paste screen-printed onto a laminated polymer film). For example, the flex-PCB may include the layer (301a) and the substrate A (309a), or the layer (303a) and the substrate B (309b). In another example, the laminated polymer film (screen-printed using silver paste) may include the layer (301a) and the substrate A (309a), or the layer (303a) and the substrate B (309b). In one or more embodiments, the layer (301a) and the layer (303a) are connected to corresponding wires of the wires (305) depicted in FIG. 3A above.

In one or more embodiments, the layer (301b) and/or layer (303b) are constructed using carbon/graphite paste or other electrically resistive material having higher resistance than the layer (301a) and/or layer (303a). For example, the layer (301b) and/or layer (303b) may be screen-printed or otherwise coated, using carbon/graphite paste or other electrically resistive material, over the flex-PCB or the laminated polymer film (with prior screen-printed silver paste). As used herein, the electrically resistive material is an electrically conductive material with higher electrical resistivity than copper or silver. In one or more embodiments, the screen-printed or coated carbon/graphite of the layer (301b) and/or layer (303b) has a thickness in the range of 5-15 micrometer (µm).

In one or more embodiments, the layer (301a) and layer (301b) may have the same nominal dimensions in both width and length directions. For example, the nominal width may be approximately 1 inch. In one or more embodiments, the layer (301b) is wider (e.g., 1.25 inch) than and overlaps the layer (301a) (e.g., 1 mm) in the width direction. In one or more embodiments, the layer (301b) is separated into sections in the length direction where each section overlaps one opening site of the openings (313) along the layer (301a). An example of the layer (301b) separated into sections is described in reference to FIG. 3C below.

In one or more embodiments, the spacer layer (311) includes openings (313). The openings (313) include a number of opening sites where each opening site corresponds to (e.g., aligned with) an overlapping region (e.g., overlapping region (302)) of the substrate A (309a) and the substrate B (309b). When the user (106) applies an external force (e.g., by lying down, sitting, or stepping) on the surface of the sensor module (201), either directly or indirectly via the padding (102), the spacer layer (311) is deformed such that the first layer electrode (301) and the second layer electrode (303) are brought together in electrical contact with each other through the openings (313) in the spacer layer (311). As noted above, more than one first layer electrode (301) and more than one second layer electrode (303) may exist in the sensor module (201). Depending on the size of the area where the user (106) applies the force onto the sensor module (201), more than one first layer electrode (301) and more than one second layer electrode (303) may be brought together in electrical contact with each other simultaneously through multiple opening sites of the openings (313) in the spacer layer (311).

In one or more embodiments, each opening site of the openings (313) defines a point of contact (referred to as a sensing point of the sensor module (201)) between the first layer electrode (301) and the second layer electrode (303). The area of electrical contact at each opening site when the force is applied to the sensor module (201) is referred to as the opening site contact area, or simply contact area. The pressure exerted between the first layer electrode (301) and the second layer electrode (303) at each opening site contact area when the force is applied to the sensor module (201) is referred to as the opening site contact pressure, or simply contact pressure. The electrical resistance between the first layer electrode (301) and the second layer electrode (303) through each opening site contact area when the force is applied to the sensor module (201) is referred to as the opening site contact resistance, or simply contact resistance.

In one or more embodiments, the contact resistance is a function of the contact pressure. For example within certain range of the contact pressure (referred to as the linear sensitivity range of contact pressure), higher contact pressure may lower the contact resistance, and lower contact pressure may increase the contact resistance. In contrast, the contact resistance may be substantially independent of the contact pressure when the contact pressure is outside of the linear sensitivity range of contact pressure. For example, the contact resistance may approach infinity when the contact pressure is less than the lower limit of the linear sensitivity range of contact pressure. In another example, the contact resistance may approach a constant when the contact pressure exceeds the upper limit of the linear sensitivity range of contact pressure. The linear sensitivity range of contact pressure, or simply linear sensitivity range, is the range of contact pressure between these lower and upper limits. The ratio of the resulting decrease in the contact resistance to an increase in contact pressure at each opening site within the linear sensitivity range is referred to as the opening site sensing sensitivity, or simply sensing sensitivity.

In one or more embodiments, one or more of the thicknesses, contact areas, and material types of the padding (102), substrate A (309a), substrate B (309b), the first layer electrode (301), the second layer electrode (303), and the spacer layer (311) are selected to enhance the sensing sensitivity. For example, the thickness and material type of the padding (102) may be selected such that throughout a predetermined weight range (e.g., 20 kg-500 kg or 44 lb-1100 lb), the weight of the user (106) is transferred into a contact pressure within the linear sensitivity range. In one or more embodiments, in addition to the functionalities of reducing noise and enhancing comfort level of the user (106), the padding (102) is further configured to transfer, collectively with the substrate A (309a) and the substrate B (309b), the weight of the user (106) into a contact pressure, in each contact area throughout the sensor module (201), that is within the linear sensitivity range.

In the example construction A or example construction B, each opening site of the openings (313) may include one or more holes each shaped as a square, rectangle, circle, dot, cross, etc. For example, each opening site may include a single square/rectangle/circle/dot/cross shaped hole. The contact area and the contact resistance are based on the single square/rectangle/circle/dot/cross shaped hole. In another example, each opening site may include multiple square/rectangle/circle/dot/cross shaped holes. The contact area and the contact resistance are based on the combined area and the combined electrical resistance of these multiple square/rectangle/circle/dot/cross shaped holes. Each hole may have an X-dimension or Y-dimension between 0.1 cm and 12 cm. Further, let L denotes the thickness of the first layer electrode (301) and/or the second layer electrode (303), and let A denotes the area of each hole, the ratio L/A is less than 12,000 in one or more embodiments. Additional example constructions are listed in TABLE 2 below. While TABLE 2 corresponds to a user weight range of 20 Kg-500 Kg, one or more embodiments may correspond to a different user weight range or a subset of the user weight range shown in TABLE 2. For example, an embodiment for a baby as the user may correspond to a user weight range of 1 Kg-10 Kg.

TABLE 2

| User weight 20 Kg-500 Kg | Example Mattress Pad | Example Mattress |
|---|---|---|
| Padding thickness (mm) | 0-20 | 0 |
| Substrate thickness (mm) | 0.025-03 | 0.025-03 |
| Spacer thickness (mm) | 0.02-3 | 0.02-3 |
| Opening contact area (cm$^2$) | 1-96 | 1-96 |
| Contact pressure (g/cm$^2$) | 5-70 | 5-70 |
| Sensitivity (Ohm/cm$^2$) | 100-100000 | 100-100000 |

Figure 3C:
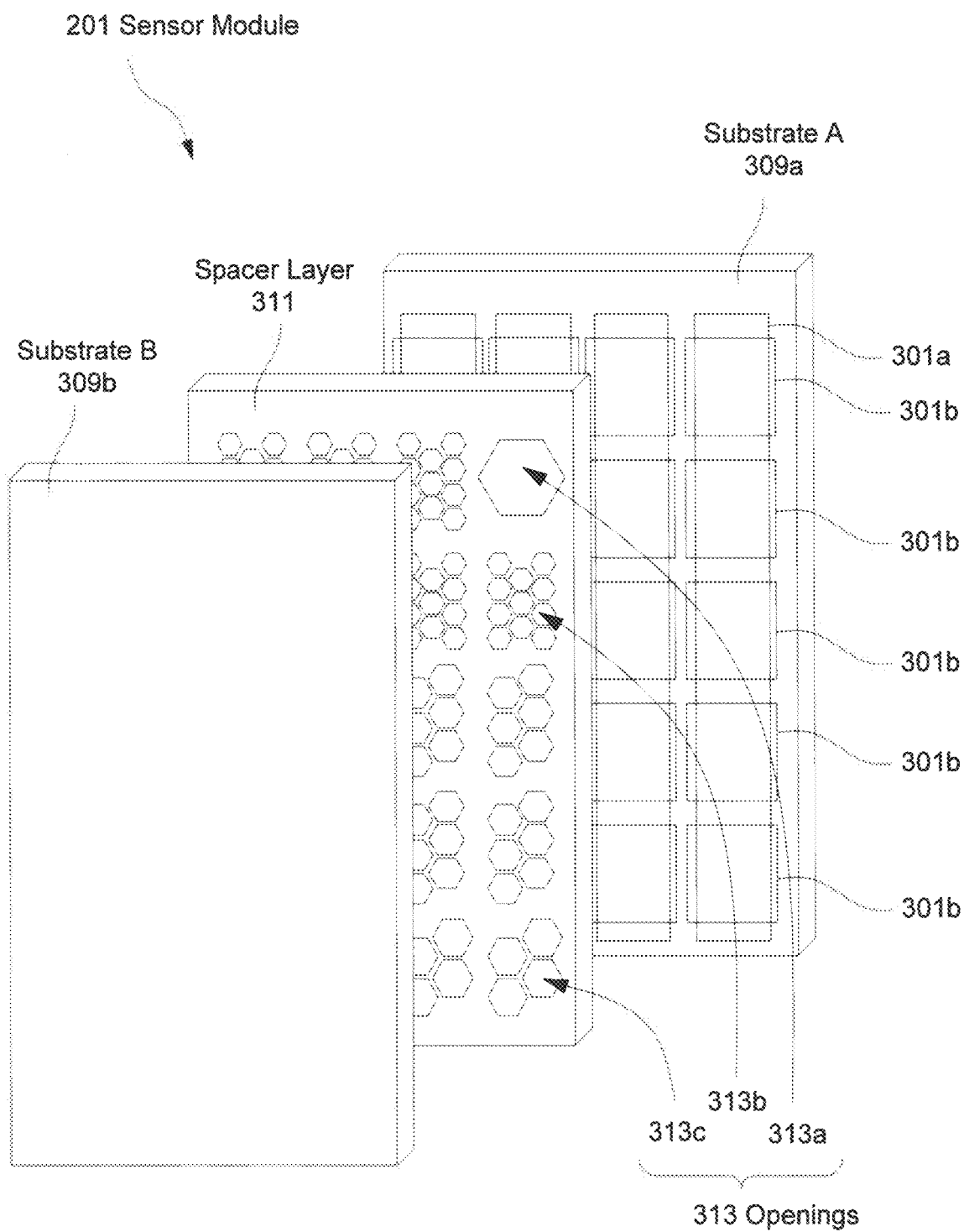
FIG. 3C shows an example perspective view of the sensor module according to one or more embodiments of the invention.

FIG. 3C shows an example perspective view of the sensor module (201) according to one or more embodiments of the invention.

In accordance with one or more embodiments, FIG. 3C shows an example of a 3D perspective view of the sensor module (201) depicted in FIGS. 3A and 3B above. In one or more embodiments, one or more of the modules and elements shown in FIG. 3C may be omitted, repeated, and/or substituted. Accordingly, embodiments of the air mattress with sensor module for patient care should not be considered limited to the specific arrangements of modules shown in FIG. 3C.

In the example shown in FIG. 3C, the layer (301b) is wider than and overlaps the layer (301a) in the width direction. Further, the layer (301b) is separated into sections in the length direction where each section overlaps one opening site of the openings (313) along the layer (301a). The openings (313) includes an example opening site A (313a) having a single hexagonal shaped hole, an example opening site B (313b) having a matrix of 11 hexagonal shaped holes, an example opening site C (313c) having a matrix of 4 hexagonal shaped holes, etc. The layer (303a) and layer (303b) are obscured by the substrate B (309b) and are not explicitly shown. Although the layer (301b) is shown as separated into sections and the openings (313) are shown as including different layouts of opening sites in the example depicted in FIG. 3C, other configurations of the layer (301b) and the openings (313) are also possible in other examples. For example, the layer (301b) may include a contiguous rectangular shape superimposing multiple opening sites of the openings (313) throughout at least a portion of the entire length of the layer (301b) while the openings (313) may include consistent layouts of opening sites throughout at least a portion of the spacer layer (311). In one or more embodiments, in addition to the pressure sensors described above, the sensor module (201) may also includes one or more temperature sensors and/or humidity sensors for generating temperature and/or humidity measurements in addition to the pressure measurements.

Figure 4:
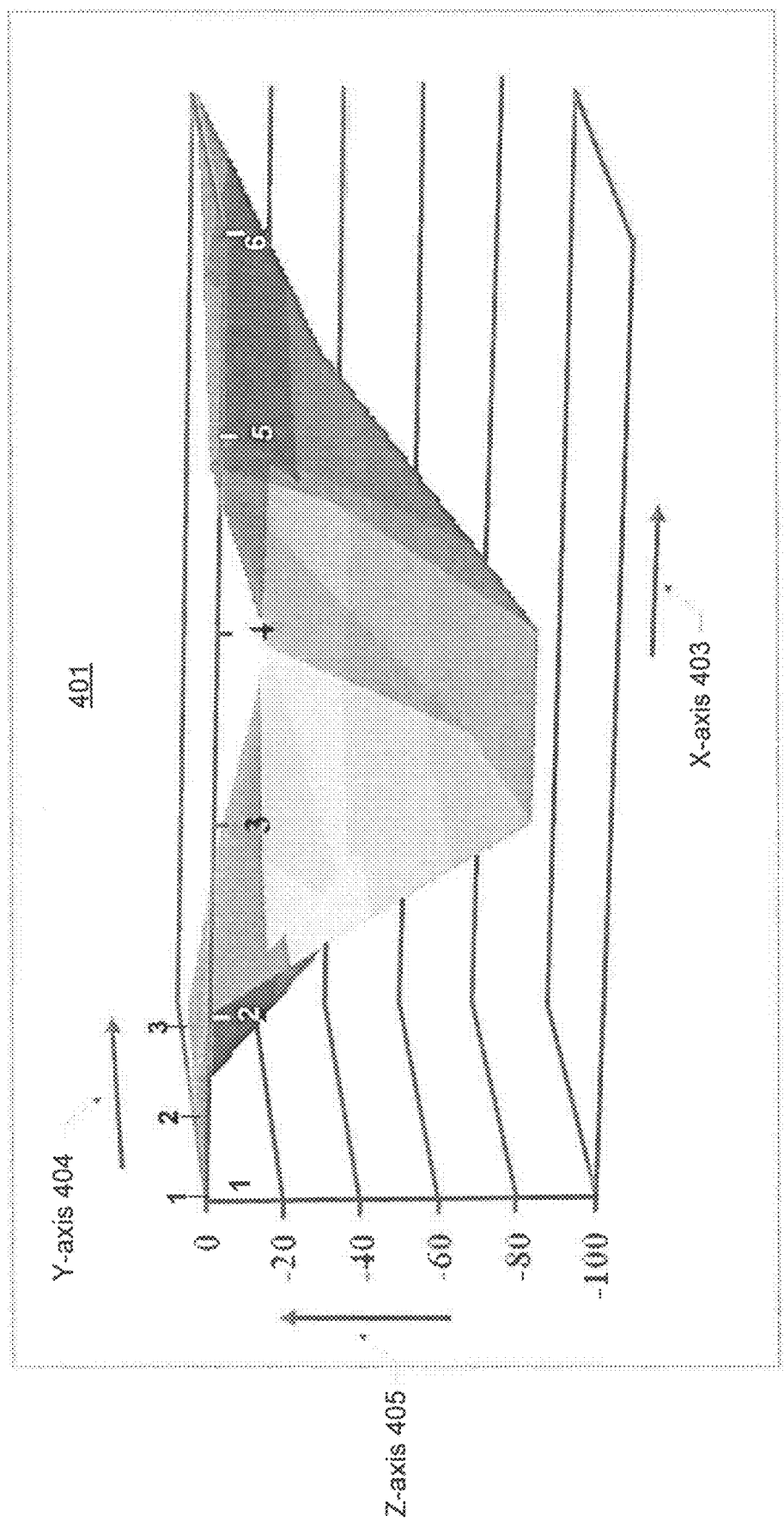
FIG. 4 shows an example graph of topographical data of the sensor module according to more or more embodiments of the present disclosure.

FIG. 4 shows an example graph of topographical data (401) of the sensor module (201) according to more or more embodiments of the present disclosure. In one or more embodiments, the output signal generated by the sensor module (201) is processed by a computing device depicted in FIG. 8A below to produce the topographical data (401) of FIG. 4. In one or more embodiments, the output signal is dependent on a contact resistance between the first layer electrode (301) and the second layer electrode (303) at the openings (313) of the spacer layer (311). In one or more embodiments, the output signal may also include one or more temperature and/or humidity measurements in addition to the contact resistance based pressure measurements. In one or more embodiments, the topographical data (401) is sent from the computing device to the controller (130a) for displaying the graph.

As shown in FIG. 4, the graph of the topographical data (401) contains three major axes: an x-axis (403), a y-axis (404), and a z-axis (405). Each of the three axes will be described below in more detail.

In one or more embodiments, the x-axis (403) and the y-axis (404) represent the 2D planar surface of the sensor module (201). Each point on the X-Y plane represents a point of contact (i.e., a sensing point) between the first layer electrode (301) and the second layer electrode (303). The number of points on each of the x-axis (403) and the y-axis (404) depends on the size of the sensor module (201). For example, in a sensor module (201) with six-by-six electrode layer array matrix, there are six data points on the x-axis (403) and six data points on the y-axis (404).

In one or more embodiments, the z-axis (405) represents a depth value that depicts a distribution of a user's weight on the surface of the sensor module (201). When a user or a user's weight presses down, directly or indirectly, on the surface of the sensor module (201) and causes a part of the first layer electrode (301) to contact a part of the second layer electrode (303) through the opening (313) in the spacer layer (311), the physical and electrical contact between the first layer electrode (301) and the second layer electrode (303) generates the output signal that is outputted from the sensor module (201) to the computing device. The computing device processes the output signal to calculate a z-axis (405) depth value. For example, the value (i.e., z-axis (405) depth value) may represent a magnitude of a sensed analog current induced by an applied voltage across a contact resistance at a sensing point of the sensor module (201). In one or more embodiments, the contact resistance decreases as the contact pressure increases at the sensing point and, therefore, the value also represents the contact pressure at the sensing point. In this context, each sensing point is a pressure sensor. For example within a certain range of contact pressure, higher contact pressure may lower the contact resistance with a substantially linear relationship between contact resistance and contact pressure.

As shown in FIG. 4, the topography data (401) is obtained from a six-by-three sensor array corresponding to x=1, 2, 3, 4, 5, 6 along the x-axis (403) and y=1, 2, 3 along the y-axis (404). As shown in FIG. 4, the user or the user's weight is applying a larger external force near the center of the x-axis (403) (corresponding to x=3, 4) and at one side of the y-axis (404) (corresponding to y=1). In other words, based on the topographical data (401) shown in FIG. 4, it is detected that a part of the user's body pressing down on the sensor module (201) is approximately at the center of one side of the sensor module (201).

In one or more embodiments, the user's posture and a movement by the user on the surface of the sensor module (201) are determined using the topographical data (401). From the movement by the user on the surface of the sensor module (201), healthcare professionals may determine changes in the user's posture, breathing rhythm, the user's frequency of cough, and other actions of the user while the user is on the sensor pad.

Figure 5A:
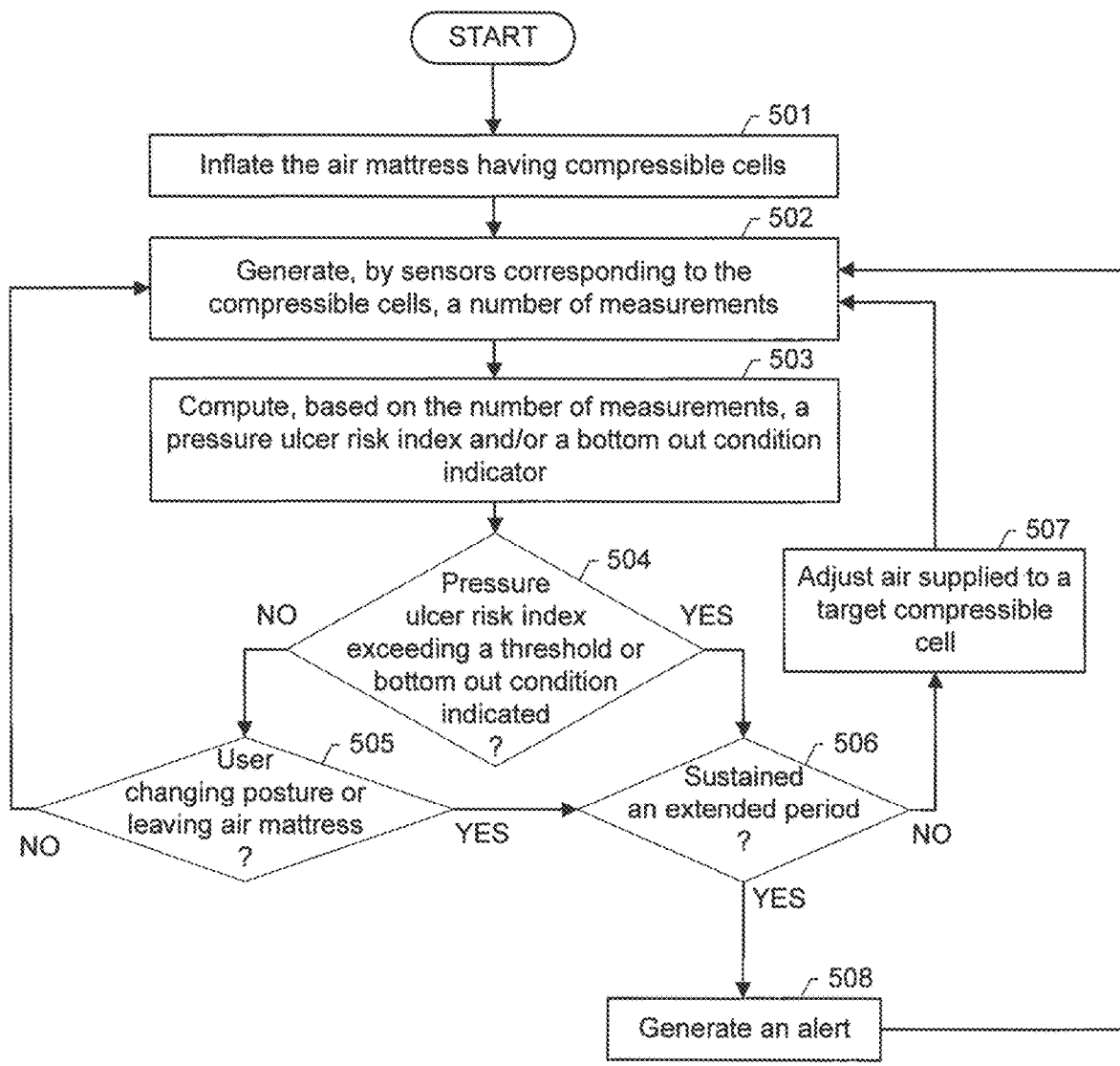
FIGS. 5A and 5B show method flow charts according to one or more embodiments of the invention.

FIG. 5A shows a flow chart of a method in accordance with one or more embodiments. For example, the method depicted in FIG. 5A may be practiced using the air mattress with sensor module for patient care described in reference to FIGS. 1A-1B, 2A-2B, 3A-3C, and 4 above. In one or more embodiments, one or more of the elements shown in FIG. 5A may be omitted, repeated, and/or performed in a different order. Accordingly, embodiments of the air mattress with sensor module for patient care should not be considered limited to the specific arrangements of elements shown in FIG. 5A.

Initially in STEP 501, compressible cells of an air mattress are inflated. In one or more embodiments, each compressible cell contacts a user of the air mattress in one of contact areas of the user based on a posture of the user. In one or more embodiments, the compressible cells are divided into compressible cell groups that are inflated independent of each other, e.g., using separate air intakes or separate air pumps.

In Step 502, a number of measurements are generated, by sensors corresponding to the compressible cells. In one or more embodiments, each measurement relates to the contact area of a corresponding compressible cell. For example, each measurement may correspond to a pressure measurement, temperature measurement, and/or humidity measurement for the contact area of the corresponding compressible cell. In one or more embodiments, a mapping is generated to associate each sensor in the sensor module to a compressible cell of the air mattress. Based on the mapping, the pressure/temperature/humidity measurement of each sensor is assigned to the corresponding compressible cell. Based on the user's posture, each compressible cell is associated with a particular contact area of the user's body. Accordingly, the pressure/temperature/humidity measurement of each sensor is associated with the corresponding contact area of the user's body.

In Step 503, a pressure ulcer risk index and/or a bottom out condition indicator are computed based on the number of measurements. In one or more embodiments, the pressure ulcer risk index represents a likelihood that the user may develop a pressure ulcer at a particular contact area due to sustained skin pressure. For example, the pressure ulcer risk index of a particular contact area of the user's body may be computed by multiplying the pressure measurement of a sensor corresponding to the contact area and a length of time during which the pressure measurement exceeds a pre-determined pressure level. In addition, the multiplication product may be adjusted higher based on the temperature and/or humidity measurement associated with the contact area exceeding a pre-determined temperature and/or humidity level. In one or more embodiments, the pressure ulcer risk index may be computed by combining (e.g., averaging or selecting the maximum value) the multiplication products, with optional temperature/humidity based adjustment, associated with multiple contact areas that are deemed as high risk areas for developing pressure ulcers. For example, the high risk areas may correspond to typical locations on the air mattress where the user's shoulder, buttock, ankle, etc. may be in contact.

In one or more embodiments, the bottom out condition indicator indicates the occurrence of the bottom out condition at one or more compressible cells. In one or more embodiments, the bottom out condition indicator may be computed by comparing the pressure measurement to a pre-determined bottom out pressure level. For example, the pre-determined bottom out pressure level may be determined based on the top surface and the bottom surface of the compressible cell coming into hard contact with each other. In one or more embodiments, the bottom out condition indicator is computed during a deflation time period of the compressible cell. In one or more embodiments, (a) the pressure ulcer risk index exceeds a pre-determined threshold and (b) the bottom out indicator indicates the occurrence of the bottom out condition are referred to as notable conditions.

In Step 504, a determination is made as to whether (a) the pressure ulcer risk index exceeds a pre-determined threshold and/or (b) the bottom out indicator indicates the occurrence of the bottom out condition. If the determination is positive, i.e., either (a) or (b) has occurred, the method proceeds to Step 506. If the determination is negative, i.e., neither (a) nor (b) has occurred, the method proceeds to Step 505.

In Step 505, the pressure measurements are further analyzed to determine if the user is changing posture or leaving the air mattress. In one or more embodiments, the user changing posture is detected based on a significant change of the pressure distribution over the air mattress. This indicates that the user's body weight is moving to different locations on the air mattress, leading to the conclusion that the user is changing posture, e.g., from the lying posture to the sitting posture. In one or more embodiments, the user leaving the air mattress is detected when all pressure measurements are less than a pre-determined low level. This indicates that the user's body weight is no longer supported by the air mattress, leading to the conclusion that the user has left the air mattress or has accidentally fallen from the air mattress. In one or more embodiments, the user changing posture or leaving the air mattress is detected based on detecting a movement of the pressure distribution over a time period (e.g., 3 seconds, 10 seconds, 1 minute, etc.). For example, a movement of the geometric centroid of the topographical data depicted in FIG. 4 above in a consistent direction over the time period (e.g., 3 seconds, 10 seconds, 1 minute, etc.) may represent the user changing posture or leaving the air mattress either intentionally or accidentally. In one or more embodiments, (a) the pressure ulcer risk index exceeds a pre-determined threshold, (b) the bottom out indicator indicates the occurrence of the bottom out condition, and (c) the user changing posture or leaving the air mattress either intentionally or accidentally are referred to as notable conditions.

If the determination in Step 505 is positive, i.e., it is determined that the user is leaving the air mattress, the method proceeds to Step 506. If the determination in Step 505 is negative, i.e., it is determined that the user is not leaving the air mattress, the method returns to Step 502.

In Step 506, a determination is made as to whether the duration of the notable condition(s) detected in Step 504 and/or Step 505 has sustained an extended time period (e.g., 3 seconds, 10 seconds, 1 minute, 10 minutes, 1 hour, etc.), referred to as the sustained duration. If the determination is negative, i.e., none of the notable condition(s) has not sustained the extended time period, the method proceeds to Step 507.

If the determination is positive, i.e., at least one notable condition has sustained the extended time period, the method proceeds to Step 508.

In Step 507, the fluid (e.g., air) supplied to a target compressible cell is adjusted to alleviate the notable condition(s). In one or more embodiments, the target compressible cell is selected from the compressible cells of the air mattress based on a pre-determined criterion. For example, the target compressible cell may correspond to the sensor whose pressure measurement is used in computing the pressure ulcer risk index and/or the bottom out condition leading to detecting the notable condition(s). In such example, the fluid (e.g., air) supplied to the target compressible cell may be decreased to alleviate the pressure ulcer risk or increased to alleviate the bottom out condition. In another example, the target compressible cell may correspond to a compressible cell that is pivotal in the user changing posture, such as the compressible cell under the user's buttock when changing between the lying posture and the sitting posture. In such example, the fluid (e.g., air) supplied to the target compressible cell may be adjusted to assist posturing changing of the user to prevent the user from leaving or accidentally rolling or falling off the air mattress during the posture changing maneuver. In yet another example, the target compressible cell may correspond to the compressible cell C (111c) depicted in FIGS. 1A and 1B above. In such example, the fluid (e.g., air) supplied to the target compressible cell may be increased to impede a lateral movement of the user to prevent the user from leaving or accidentally rolling or falling off the air mattress.

In one or more embodiments, the target compressible cell may belong to a compressible cell group. In such embodiments, adjusting the fluid (e.g., air) supplied to the target compressible cell is performed by adjusting the fluid (e.g., air) supplied to the compressible cell group that the target compressible cell belongs. Upon completing the fluid (e.g., air) supply adjustment to the target compressible cell, the method returns to Step 502.

In Step 508, an alert is generated in response to detecting at least one notable condition sustained over the extended period. In one or more embodiments, the alert is sent to a care taker of the user. Accordingly, the care taker may perform appropriate actions. For example, the alert may be displayed on the controller (130*a*) depicted in FIG. 2A above. In another example, the alert may be generated by a cloud based computing resource and sent to or retrieved by the care taker's device for display. The care taker's device may be a mobile device or a desktop device remote from the air mattress.

An example of performing the flow chart depicted in FIG. 1A above is described in reference to FIGS. 6 and 7 below.

Figure 5B:
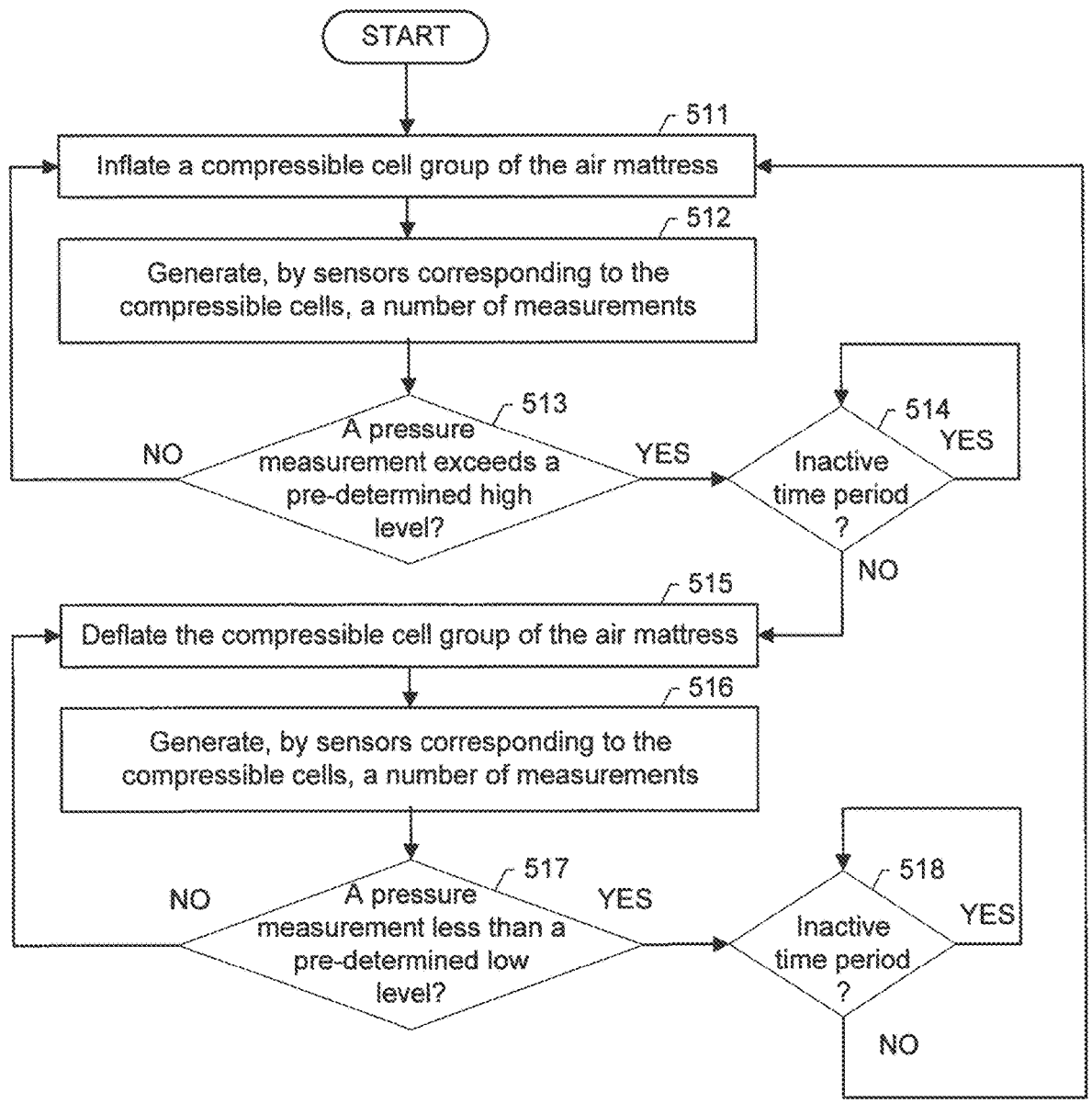

FIG. 5B shows a flow chart of a method in accordance with one or more embodiments. For example, the method depicted in FIG. 5B may be practiced using the air mattress with sensor module for patient care described in reference to FIGS. 1A-1B, 2A-2B, 3A-3C, and 4 above. In one or more embodiments, one or more of the elements shown in FIG. 5B may be omitted, repeated, and/or performed in a different order. Accordingly, embodiments of the air mattress with sensor module for patient care should not be considered limited to the specific arrangements of elements shown in FIG. 5B.

Initially in Step 511, a compressible cell group of an air mattress is inflated. In one or more embodiments, multiple compressible cell groups are inflated independent of each other, e.g., using separate air intakes or separate air pumps according to different inflation time schedules.

In Step 512, a number of measurements are generated, by sensors corresponding to the compressible cells in the compressible cell group. In one or more embodiments, each measurement relates to the contact area of a corresponding compressible cell. For example, each measurement may correspond to a pressure measurement, temperature measurement, and/or humidity measurement for the contact area of the corresponding compressible cell. In one or more embodiments, a mapping is generated to associate each sensor in the sensor module to a compressible cell of the compressible cell group. Based on the mapping, the pressure/temperature/humidity measurement of each sensor is assigned to the corresponding compressible cell. Based on the user's posture, each compressible cell is associated with a particular contact area of the user's body. Accordingly, the pressure/temperature/humidity measurement of each sensor is associated with the corresponding contact area of the user's body.

In Step 513, a determination is made as to whether a measurement exceeds a pre-determined high level. Each pressure measurement associated with each corresponding compressible cell in the compressible cell group is compared to the pre-determined high level for making the determination. In one or more embodiments, the determination is based on at least one pressure measurement exceeding the pre-determined high level. In one or more embodiments, the determination is based on all pressure measurements exceeding the pre-determined high level. If the determination is positive, i.e., the measurement has exceeded the pre-determined high level, the method proceeds to Step 514. If the determination is negative, i.e., the measurement has not exceeded the pre-determined high level, the method returns to Step 511.

In Step 514, a timing loop is executed to wait for a pre-determined time period, referred to as the inactive time period. When the inactive time period has elapsed, the method proceeds to Step 515.

In Step 515, the compressible cell group inflated in Step 511 is deflated. In one or more embodiments, multiple compressible cell groups are deflated independent of each other, e.g., using separate air intakes or separate air pumps according to different deflation time schedules.

In Step 516, a number of measurements are generated for the compressible cell group in substantially the same way as Step 512.

In Step 517, a determination is made as to whether a measurement is less than a pre-determined low level. Each pressure measurement associated with each corresponding compressible cell in the compressible cell group is compared to the pre-determined low level for making the determination. In one or more embodiments, the determination is based on at least one pressure measurement being less than the pre-determined low level. In one or more embodiments, the determination is based on all pressure measurements being less than the pre-determined low level. If the determination is positive, i.e., the measurement is less than the pre-determined low level, the method proceeds to Step 518. If the determination is negative, i.e., the measurement is not less than the pre-determined low level, the method returns to Step 515.

In Step 518, a timing loop is executed to wait for a pre-determined time period, referred to as the inactive time period. When the inactive time period has elapsed, the method returns to Step 511.

In one or more embodiments, the pressure ulcer risk of the user is reduced by alternating between inflation and deflation of adjacent compressible cell groups using the method described above. In one or more embodiments, alternating between inflation and deflation of a compressible cell group using the method described above based on pressure measurements prevents the bottom out condition from occurring.

An example of performing the flow chart depicted in FIG. 1B above is described in reference to FIGS. 6 and 7 below.

Figure 6:
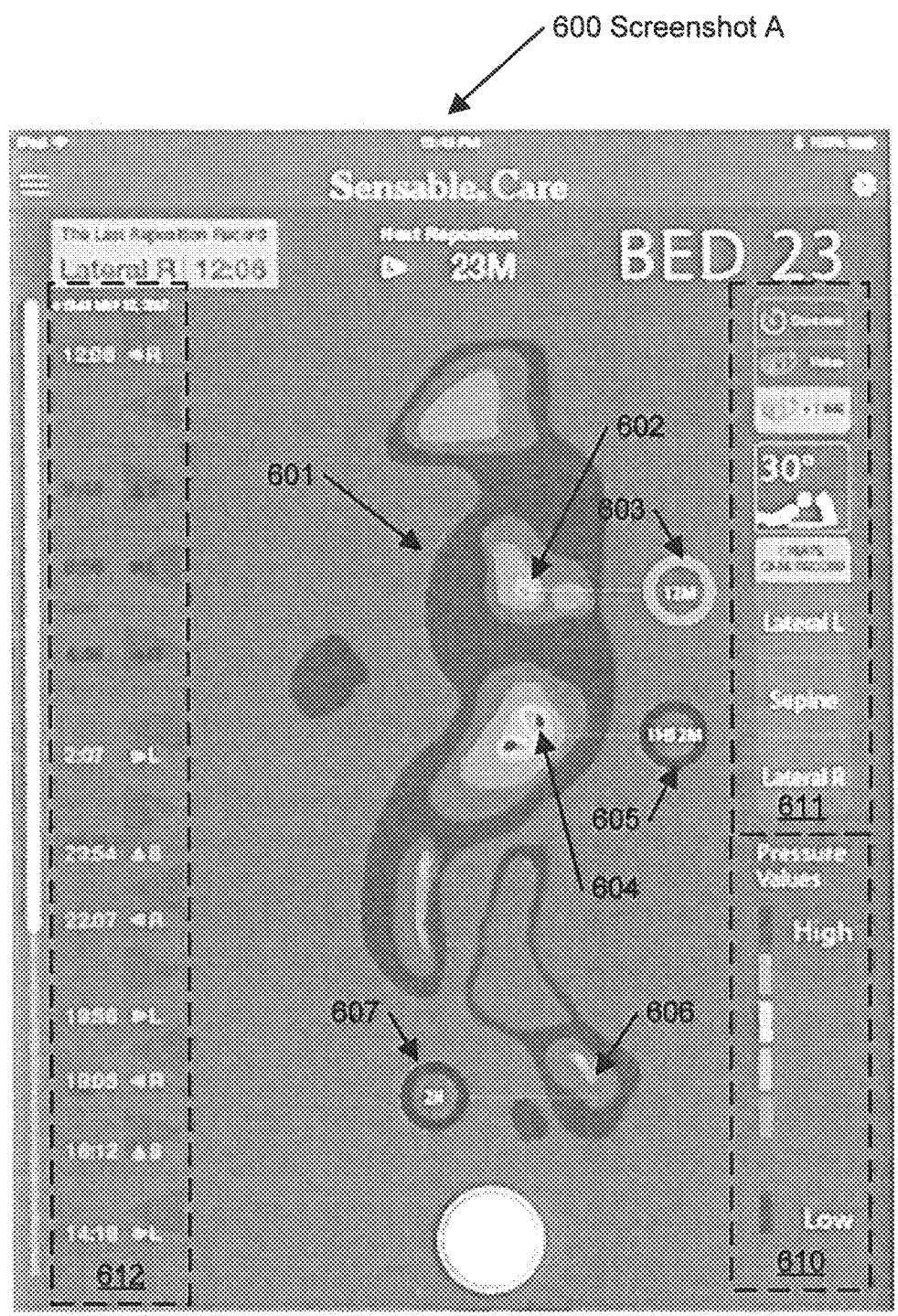
FIGS. 6 and 7 show example display screenshots according to one or more embodiments of the invention.

FIG. 6 shows an example screenshot A (600) in accordance with one or more embodiments. For example, the example screenshot A (600) depicted in FIG. 6 may be generated using the air mattress with sensor module for patient care described in reference to FIGS. 1A-1B, 2A-2B, 3A-3C, and 4 above. In one or more embodiments, one or more of the elements shown in FIG. 6 may be omitted, repeated, and/or organized in a different order. Accordingly, embodiments of the air mattress with sensor module for patient care should not be considered limited to the specific arrangements of elements shown in FIG. 6.

In one or more embodiments, the example screenshot A (600) is displayed on the controller (130*a*) depicted in FIG. 2A above. In one or more embodiments, the example screenshot A (600) is displayed on a device used by a healthcare professional. In particular, the device is used to access the cloud computing resource that exchange data and other information with the controller (130*a*) depicted in FIG. 2A above.

As shown in FIG. 6, the screenshot A (600) includes a pressure distribution (601) where the pressure measurements across the air mattress are represented by shading according to the scale (610). In particular, the pressure distribution (601) includes high pressure contact areas (602), (604), and (606) where corresponding pressure measurements (603), (605), and (607) are annotated. In one or more embodiments, the pressure distribution (601) is generated by individual pressure measurements from a sensor module having a large number of sensors (e.g., 50 columns by 100 rows) such that the pressure distribution (601) appears visually continuous. In one or more embodiments, the pressure distribution (601) is generated by interpolating individual pressure measurements from a sensor module having a modest number of sensors (e.g., 10 columns by 20 rows) such that the pressure distribution (601) appears visually continuous. In one or more embodiments, the pressure measurements are performed on repetitive basis using the method described in reference to FIG. 5A above. In such embodiments, the high pressure contact areas (602), (604), and (606) correspond to where the aforementioned notable conditions exist. For example, the high pressure contact area (602) may correspond to a high pressure ulcer risk index. In another example, the high pressure contact area (604) may correspond to a bottom out condition. In yet another example, the high pressure contact area (606) may show a consistent movement and correspond to the user changing posture or leaving the air mattress.

In one or more embodiments, pressure of target compressible cells are adjusted based on notable conditions using the method described in reference to FIG. 5A above. For example, the compressible cell corresponding to the high pressure contact area (602) may incrementally deflate to reduce pressure ulcer risk. In another example, the compressible cell corresponding to the high pressure contact area (604) may incrementally inflate to alleviate the bottom out condition.

In one or more embodiments, notable conditions are logged and displayed as the notable condition history (612). Control functions and status of the air pump and other mechanisms of the bed are displayed in the menu (611). Using the menu (611), the care taker may perform adjustment in response to viewing the pressure distribution (601) and the notable condition history (612).

Figure 7:
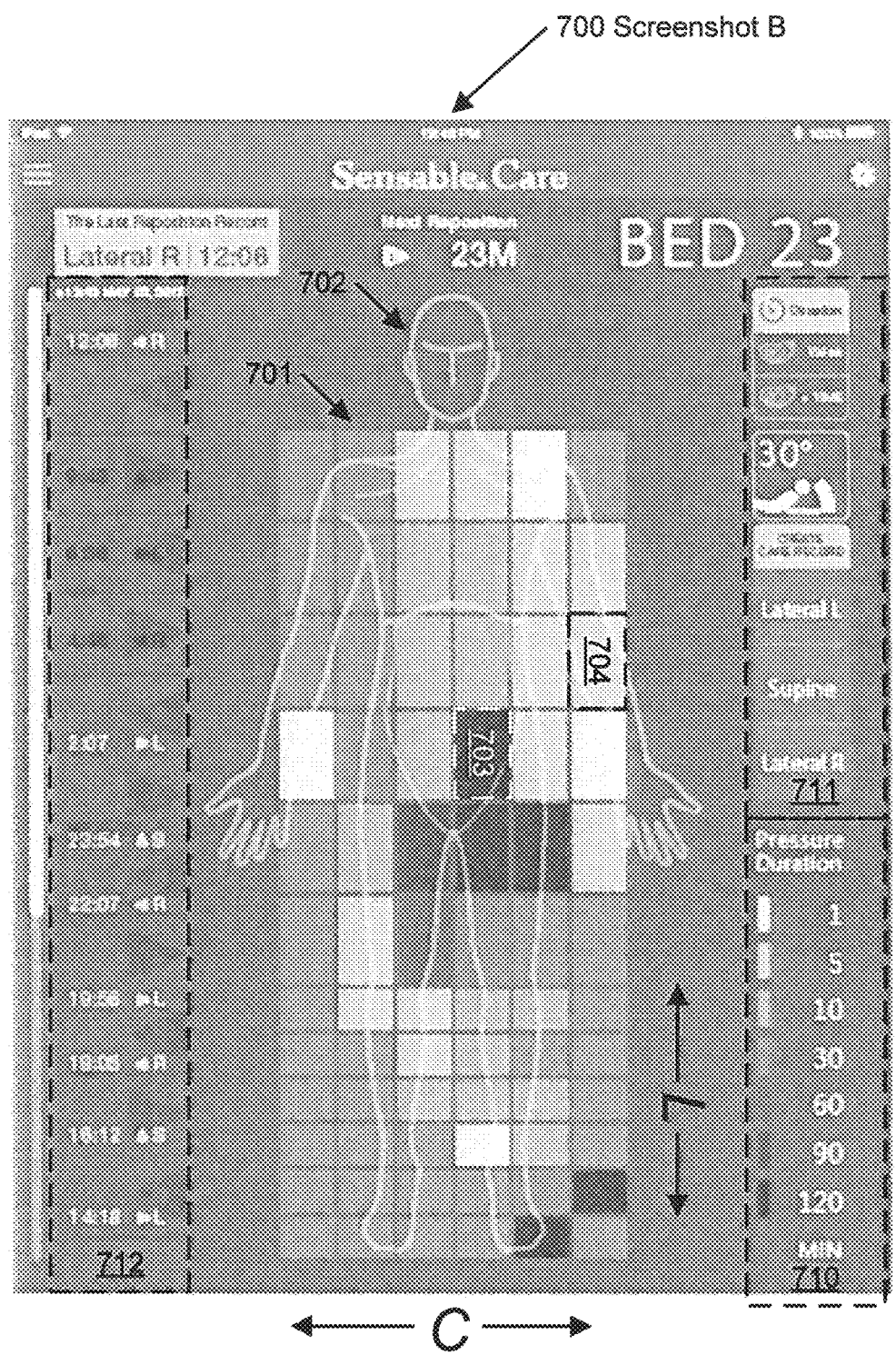

FIG. 7 shows an example screenshot B (700) in accordance with one or more embodiments. For example, the example screenshot B (700) depicted in FIG. 7 may be generated using the air mattress with sensor module for patient care described in reference to FIGS. 1A-1B, 2A-2B, 3A-3C, and 4 above. In one or more embodiments, one or more of the elements shown in FIG. 7 may be omitted, repeated, and/or organized in a different order. Accordingly, embodiments of the air mattress with sensor module for patient care should not be considered limited to the specific arrangements of elements shown in FIG. 7.

In one or more embodiments, the example screenshot B (700) is displayed on the controller (130a) depicted in FIG. 2A above. In one or more embodiments, the example screenshot B (700) is displayed on a device used by a healthcare professional. In particular, the device is used to access the cloud computing resource that exchange data and other information with the controller (130a) depicted in FIG. 2A above.

As shown in FIG. 7, the screenshot B (700) includes a pressure duration map (701) superimposing an outline (702) of a user's body lying on the air mattress. In one or more embodiments, the outline (702) may be generated based on the pressure distribution (601) depicted in FIG. 6 above. In one or more embodiments, the pressure duration map (701) is divided into a grid having multiple columns along the longitudinal direction of the user (denoted as "L") and multiple rows along the sideways direction of the user (denoted as "C"). The shading of each divided section (e.g., section (703), section (704), etc.) in the pressure duration map (701) represents, according to the scale (710), the length of time that the pressure measurement associated with the divided section has exceeded a pre-determined level. In one or more embodiments, the pre-determined level corresponds to a skin pressure level above which the risk of developing a pressure ulcer is increased. For example, the pressure measurement of the section (703) has exceeded the pre-determined level for approximately 120 minutes indicating high pressure ulcer risk. The pressure measurement of the section (704) has exceeded the pre-determined level for approximately 10 minutes indicating nominal pressure ulcer risk.

In one or more embodiments, each column of the pressure duration map (701) corresponds to a compressible cell in top view (200) depicted in FIG. 1B above. In one or more embodiments, the rows and columns of the pressure duration map (701) correspond to the rows and columns of compressible cells in the example (420) depicted in FIG. 2B above. In one or more embodiments, the compressible cells associated with odd numbered columns of the pressure duration map (701) belong to a compressible cell group (referred to the odd compressible cell group) while the compressible cells associated with even numbered columns of the pressure duration map (701) belong to another compressible cell group (referred to the even compressible cell group). The odd and even compressible cell groups may be inflated and deflated in alternating sequence of recurring time periods to reduce the pressure duration experienced by the user. In particular, a larger fraction of the body weight of the user is supported by the odd compressible cell group when the odd compressible cell group is being inflated while the even compressible cell group is being deflated. In contrast, a larger fraction of the body weight of the user is supported by the even compressible cell group when the odd compressible cell group is being deflated while the even compressible cell group is being inflated. In one or more embodiments, inflating/deflating the odd and even compressible cell groups are performed using the method described in reference to FIG. 5B above. Using such method, the inflation and deflation time periods are determined based on the pressure measurements to prevent over-deflation/under-inflation that may result in bottom out conditions.

In one or more embodiments, notable conditions are logged and displayed as the notable condition history (712). Control functions and status of the air pump and other mechanisms of the bed are displayed in the menu (711). Using the menu (711), the care taker may perform adjustments in response to viewing the pressure duration map (701) and the notable condition history (712).

Figure 8A:
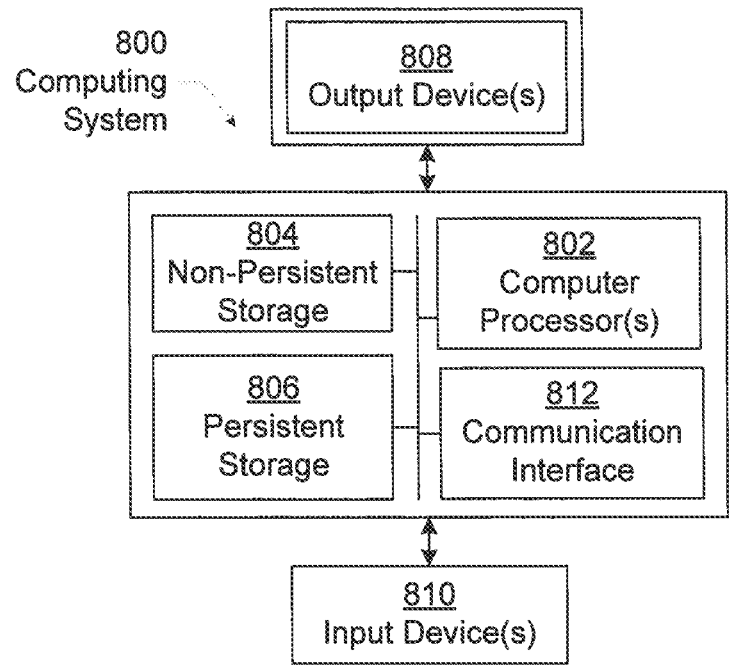
FIGS. 8A and 8B show a computing system according to one or more embodiments of the invention.

Embodiments may be implemented on a computing system. Any combination of mobile, desktop, server, router, switch, embedded device, or other types of hardware may be used. For example, as shown in FIG. 8A, the computing system (800) may include one or more computer processors (802), non-persistent storage (804) (e.g., volatile memory, such as random access memory (RAM), cache memory), persistent storage (806) (e.g., a hard disk, an optical drive such as a compact disk (CD) drive or digital versatile disk (DVD) drive, a flash memory, etc.), a communication interface (812) (e.g., Bluetooth interface, infrared interface, network interface, optical interface, etc.), and numerous other elements and functionalities.

The computer processor(s) (802) may be an integrated circuit for processing instructions. For example, the computer processor(s) may be one or more cores or micro-cores of a processor. The computing system (800) may also include one or more input devices (810), such as a touchscreen, keyboard, mouse, microphone, touchpad, electronic pen, or any other type of input device.

The communication interface (812) may include an integrated circuit for connecting the computing system (800) to a network (not shown) (e.g., a local area network (LAN), a wide area network (WAN) such as the Internet, mobile network, or any other type of network) and/or to another device, such as another computing device.

Further, the computing system (800) may include one or more output devices (808), such as a screen (e.g., a liquid crystal display (LCD), a plasma display, touchscreen, cathode ray tube (CRT) monitor, projector, or other display device), a printer, external storage, or any other output device. One or more of the output devices may be the same or different from the input device(s). The input and output device(s) may be locally or remotely connected to the computer processor(s) (802), non-persistent storage (804), and persistent storage (806). Many different types of computing systems exist, and the aforementioned input and output device(s) may take other forms.

Software instructions in the form of computer readable program code to perform embodiments of the invention may be stored, in whole or in part, temporarily or permanently, on a non-transitory computer readable medium such as a CD, DVD, storage device, a diskette, a tape, flash memory, physical memory, or any other computer readable storage medium. Specifically, the software instructions may correspond to computer readable program code that, when executed by a processor(s), is configured to perform one or more embodiments of the invention.

Figure 8B:
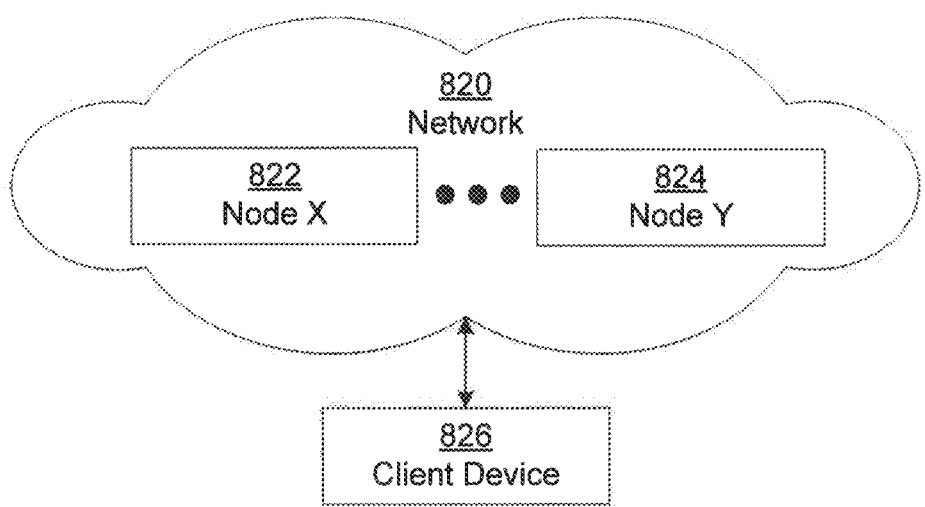

The computing system (800) in FIG. 8A may be connected to or be a part of a network. For example, as shown in FIG. 8B, the network (820) may include multiple nodes (e.g., node X (822), node Y (824)). Each node may correspond to a computing system, such as the computing system shown in FIG. 8A, or a group of nodes combined may correspond to the computing system shown in FIG. 8A. By way of an example, embodiments of the invention may be implemented on a node of a distributed system that is connected to other nodes. By way of another example, embodiments of the invention may be implemented on a distributed computing system having multiple nodes, where each portion of the invention may be located on a different node within the distributed computing system. Further, one or more elements of the aforementioned computing system (800) may be located at a remote location and connected to the other elements over a network.

Although not shown in FIG. 8B, the node may correspond to a blade in a server chassis that is connected to other nodes via a backplane. By way of another example, the node may correspond to a server in a data center. By way of another example, the node may correspond to a computer processor or micro-core of a computer processor with shared memory and/or resources.

The nodes (e.g., node X (822), node Y (824)) in the network (820) may be configured to provide services for a client device (826). For example, the nodes may be part of a cloud computing system. The nodes may include functionality to receive requests from the client device (826) and transmit responses to the client device (826). The client device (826) may be a computing system, such as the computing system shown in FIG. 8A. Further, the client device (826) may include and/or perform all or a portion of one or more embodiments of the invention.

The computing system or group of computing systems described in FIGS. 8A and 8B may include functionality to perform a variety of operations disclosed herein. For example, the computing system(s) may perform communication between processes on the same or different system. A variety of mechanisms, employing some form of active or passive communication, may facilitate the exchange of data between processes on the same device. Examples representative of these inter-process communications include, but are not limited to, the implementation of a file, a signal, a socket, a message queue, a pipeline, a semaphore, shared memory, message passing, and a memory-mapped file. Further details pertaining to a couple of these non-limiting examples are provided below.

Based on the client-server networking model, sockets may serve as interfaces or communication channel endpoints enabling bidirectional data transfer between processes on the same device. Foremost, following the client-server networking model, a server process (e.g., a process that provides data) may create a first socket object. Next, the server process binds the first socket object, thereby associating the first socket object with a unique name and/or address. After creating and binding the first socket object, the server process then waits and listens for incoming connection requests from one or more client processes (e.g., processes that seek data). At this point, when a client process wishes to obtain data from a server process, the client process starts by creating a second socket object. The client process then proceeds to generate a connection request that includes at least the second socket object and the unique name and/or address associated with the first socket object. The client process then transmits the connection request to the server process. Depending on availability, the server process may accept the connection request, establishing a communication channel with the client process, or the server process, busy in handling other operations, may queue the connection request in a buffer until server process is ready. An established connection informs the client process that communications may commence. In response, the client process may generate a data request specifying the data that the client process wishes to obtain. The data request is subsequently transmitted to the server process. Upon receiving the data request, the server process analyzes the request and gathers the requested data. Finally, the server process then generates a reply including at least the requested data and transmits the reply to the client process. The data may be transferred, more commonly, as datagrams or a stream of characters (e.g., bytes).

Shared memory refers to the allocation of virtual memory space in order to substantiate a mechanism for which data may be communicated and/or accessed by multiple processes. In implementing shared memory, an initializing process first creates a shareable segment in persistent or non-persistent storage. Post creation, the initializing process then mounts the shareable segment, subsequently mapping the shareable segment into the address space associated with the initializing process. Following the mounting, the initializing process proceeds to identify and grant access permission to one or more authorized processes that may also write and read data to and from the shareable segment. Changes made to the data in the shareable segment by one process may immediately affect other processes, which are also linked to the shareable segment. Further, when one of the authorized processes accesses the shareable segment, the shareable segment maps to the address space of that authorized process. Often, only one authorized process may mount the shareable segment, other than the initializing process, at any given time.

Other techniques may be used to share data, such as the various data described in the present application, between processes without departing from the scope of the invention. The processes may be part of the same or different application and may execute on the same or different computing system.

Rather than or in addition to sharing data between processes, the computing system performing one or more embodiments of the invention may include functionality to receive data from a user. For example, in one or more embodiments, a user may submit data via a graphical user interface (GUI) on the user device. Data may be submitted via the graphical user interface by a user selecting one or more graphical user interface widgets or inserting text and other data into graphical user interface widgets using a touchpad, a keyboard, a mouse, or any other input device. In response to selecting a particular item, information regarding the particular item may be obtained from persistent or non-persistent storage by the computer processor. Upon selection of the item by the user, the contents of the obtained data regarding the particular item may be displayed on the user device in response to the user's selection.

By way of another example, a request to obtain data regarding the particular item may be sent to a server operatively connected to the user device through a network. For example, the user may select a uniform resource locator (URL) link within a web client of the user device, thereby initiating a Hypertext Transfer Protocol (HTTP) or other protocol request being sent to the network host associated with the URL. In response to the request, the server may extract the data regarding the particular selected item and send the data to the device that initiated the request. Once the user device has received the data regarding the particular item, the contents of the received data regarding the particular item may be displayed on the user device in response to the user's selection. Further to the above example, the data received from the server after selecting the URL link may provide a web page in Hyper Text Markup Language (HTML) that may be rendered by the web client and displayed on the user device.

Once data is obtained, such as by using techniques described above or from storage, the computing system, in performing one or more embodiments of the invention, may extract one or more data items from the obtained data. For example, the extraction may be performed as follows by the computing system in FIG. 8A. First, the organizing pattern (e.g., grammar, schema, layout) of the data is determined, which may be based on one or more of the following: position (e.g., bit or column position, Nth token in a data stream, etc.), attribute (where the attribute is associated with one or more values), or a hierarchical/tree structure (consisting of layers of nodes at different levels of detail—such as in nested packet headers or nested document sections). Then, the raw, unprocessed stream of data symbols is parsed, in the context of the organizing pattern, into a stream (or layered structure) of tokens (where each token may have an associated token "type").

Next, extraction criteria are used to extract one or more data items from the token stream or structure, where the extraction criteria are processed according to the organizing pattern to extract one or more tokens (or nodes from a layered structure). For position-based data, the token(s) at the position(s) identified by the extraction criteria are extracted. For attribute/value-based data, the token(s) and/or node(s) associated with the attribute(s) satisfying the extraction criteria are extracted. For hierarchical/layered data, the token(s) associated with the node(s) matching the extraction criteria are extracted. The extraction criteria may be as simple as an identifier string or may be a query presented to a structured data repository (where the data repository may be organized according to a database schema or data format, such as XML).

The extracted data may be used for further processing by the computing system. For example, the computing system of FIG. 8A, while performing one or more embodiments of the invention, may perform data comparison. Data comparison may be used to compare two or more data values (e.g., A, B). For example, one or more embodiments may determine whether $A>B$, $A=B$, $A!=B$, $A<B$, etc. The comparison may be performed by submitting A, B, and an opcode specifying an operation related to the comparison into an arithmetic logic unit (ALU) (i.e., circuitry that performs arithmetic and/or bitwise logical operations on the two data values). The ALU outputs the numerical result of the operation and/or one or more status flags related to the numerical result. For example, the status flags may indicate whether the numerical result is a positive number, a negative number, zero, etc. By selecting the proper opcode and then reading the numerical results and/or status flags, the comparison may be executed. For example, in order to determine if $A>B$, B may be subtracted from A (i.e., $A-B$), and the status flags may be read to determine if the result is positive (i.e., if $A>B$, then $A-B>0$). In one or more embodiments, B may be considered a threshold, and A is deemed to satisfy the threshold if $A=B$ or if $A>B$, as determined using the ALU. In one or more embodiments of the invention, A and B may be vectors, and comparing A with B requires comparing the first element of vector A with the first element of vector B, the second element of vector A with the second element of vector B, etc. In one or more embodiments, if A and B are strings, the binary values of the strings may be compared.

The computing system in FIG. 8A may implement and/or be connected to a data repository. For example, one type of data repository is a database. A database is a collection of information configured for ease of data retrieval, modification, re-organization, and deletion. Database Management System (DBMS) is a software application that provides an interface for users to define, create, query, update, or administer databases.

The user, or software application, may submit a statement or query into the DBMS. Then the DBMS interprets the statement. The statement may be a select statement to request information, update statement, create statement, delete statement, etc. Moreover, the statement may include parameters that specify data, or data container (database, table, record, column, view, etc.), identifier(s), conditions (comparison operators), functions (e.g. join, full join, count, average, etc.), sort (e.g. ascending, descending), or others. The DBMS may execute the statement. For example, the DBMS may access a memory buffer, a reference or index a file for read, write, deletion, or any combination thereof, for responding to the statement. The DBMS may load the data from persistent or non-persistent storage and perform computations to respond to the query. The DBMS may return the result(s) to the user or software application.

The computing system of FIG. 8A may include functionality to present raw and/or processed data, such as results of comparisons and other processing. For example, presenting data may be accomplished through various presenting methods. Specifically, data may be presented through a user interface provided by a computing device. The user interface may include a GUI that displays information on a display device, such as a computer monitor or a touchscreen on a handheld computer device. The GUI may include various GUI widgets that organize what data is shown as well as how data is presented to a user. Furthermore, the GUI may present data directly to the user, e.g., data presented as actual data values through text, or rendered by the computing device into a visual representation of the data, such as through visualizing a data model.

For example, a GUI may first obtain a notification from a software application requesting that a particular data object be presented within the GUI. Next, the GUI may determine a data object type associated with the particular data object, e.g., by obtaining data from a data attribute within the data object that identifies the data object type. Then, the GUI may determine any rules designated for displaying that data object type, e.g., rules specified by a software framework for a data object class or according to any local parameters defined by the GUI for presenting that data object type. Finally, the GUI may obtain data values from the particular data object and render a visual representation of the data values within a display device according to the designated rules for that data object type.

Data may also be presented through various audio methods. In particular, data may be rendered into an audio format and presented as sound through one or more speakers operably connected to a computing device.

Data may also be presented to a user through haptic methods. For example, haptic methods may include vibrations or other physical signals generated by the computing system. For example, data may be presented to a user using a vibration generated by a handheld computer device with a predefined duration and intensity of the vibration to communicate the data.

The above description of functions present only a few examples of functions performed by the computing system of FIG. 8A and the nodes and/or client device in FIG. 8B. Other functions may be performed using one or more embodiments of the invention.

While one or more embodiments have been described with respect to a limited number of embodiments, those skilled in the art, having benefit of this disclosure, will appreciate that other embodiments may be devised which do not depart from the scope as disclosed herein. Accordingly, the scope should be limited only by the attached claims.

What is claimed is:

1. A mattress for patient care, comprising:
a plurality of compressible cells each configured to:
contact, when inflated, a user in a contact area of a plurality of contact areas of the user;
a plurality of sensors corresponding to the plurality of compressible cells and configured to:
generate a plurality of measurements, wherein each of the plurality of measurements relates to the contact area of a corresponding compressible cell; and
send the plurality of measurements to a pressure control device; and
the pressure control device configured to:
select, based on the plurality of measurements, a target compressible cell from the plurality of compressible cells; and
adjust, in response to the selecting, an inflation state of the selected target compressible cell.

2. The mattress of claim 1, further comprising the pressure control device configured to:
supply air to inflate the plurality of compressible cells based on the plurality of measurements; and
release the air to adjust an inflation level of the plurality of compressible cells based on the plurality of measurements.

3. The mattress of claim 1, wherein inflating the plurality of compressible cells based on the plurality of measurements comprises:
computing, based on the plurality of measurements, a pressure ulcer risk index;
iteratively selecting, in response to the pressure ulcer risk index exceeding a pre-determined threshold, a target compressible cell from the plurality of compressible cells based on a pre-determined criterion for reducing the pressure ulcer risk index; and
iteratively adjusting, in response to the pressure ulcer risk index exceeding the pre-determined threshold, the air supplied to the target compressible cell to alleviate a pressure ulcer risk,
wherein said each of the plurality of measurements comprises a contact pressure measurement in the contact area.

4. The mattress of claim 3,
wherein the plurality of sensors are disposed between the user and the plurality of compressible cells, and
wherein the plurality of measurements comprises at least one selected from a group consisting of a pressure measurement, a temperature measurement and a humidity measurement of the contact area.

5. The mattress of claim 3, further comprising:
detecting a sustained duration of the pressure ulcer risk index exceeding the pre-determined threshold; and
generating, in response to the detecting, an alert to a care taker of the user.

6. The mattress of claim 1, wherein inflating the plurality of compressible cells based on the plurality of measurements comprises:
computing, based on the plurality of measurements, an indication of the user leaving the mattress;
selecting, in response to the indication of the user leaving the mattress, a target compressible cell from the plurality of compressible cells based on a pre-determined criterion for retaining the user on the mattress; and
adjusting the air supplied to the target compressible cell to facilitate retaining the user on the mattress.

7. The mattress of claim 6, further comprising:
detecting a sustained duration of the indication of the user leaving the mattress; and
generating, in response to the detecting, an alert to a care taker of the user.

8. The mattress of claim 1, wherein inflating the plurality of compressible cells based on the plurality of measurements comprises:
detecting, based on the plurality of measurements, an indication of the user changing posture;
selecting, in response to the indication of the user changing posture, a target compressible cell from the plurality of compressible cells based on a pre-determined criterion for assisting the user changing posture; and
adjusting the air supplied to the target compressible cell to assist the user changing posture.

9. The mattress of claim 1, wherein inflating the plurality of compressible cells based on the plurality of measurements comprises:
detecting, based on the plurality of measurements, a bottom out condition of a target compressible cell of the plurality of compressible cells; and
adjusting the air supplied to the target compressible cell to alleviate the bottom out condition.

10. The mattress of claim 1,
wherein the plurality of compressible cells are coupled to form a compressible cell sheet,
wherein the plurality of sensors are coupled to form a sensor sheet, and
wherein the sensor sheet is coupled to the compressible cell sheet to maintain a corresponding relationship between the plurality of compressible cells and the plurality of sensors.

11. A bed for patient care, comprising:
a plurality of compressible cells each configured to:
  contact, when inflated, a user in a contact area of a plurality of contact areas of the user;
a plurality of sensors corresponding to the plurality of compressible cells and configured to:
  generate a plurality of measurements, wherein each of the plurality of measurements relates to the contact area of a corresponding compressible cell; and
  send the plurality of measurements to a pressure control device;
the pressure control device configured to:
  select, based on the plurality of measurements, a target compressible cell from the plurality of compressible cells; and
  adjust, in response to the selecting, an inflation state of the selected target compressible cell; and
a bed frame configured to support the user lying on the plurality of compressible cells.

12. The bed of claim 11, further comprising the pressure control device configured to:
supply air to inflate the plurality of compressible cells based on the plurality of measurements; and
release the air to adjust an inflation level of the plurality of compressible cells based on the plurality of measurements.

13. The bed of claim 11, wherein inflating the plurality of compressible cells based on the plurality of measurements comprises:
computing, based on the plurality of measurements, a pressure ulcer risk index;
iteratively selecting, in response to the pressure ulcer risk index exceeding a pre-determined threshold, a target compressible cell from the plurality of compressible cells based on a pre-determined criterion for reducing the pressure ulcer risk index; and
iteratively adjusting, in response to the pressure ulcer risk index exceeding the pre-determined threshold, the air supplied to the target compressible cell to alleviate a pressure ulcer risk,
wherein said each of the plurality of measurements comprises a contact pressure measurement in the contact area.

14. The bed of claim 13,
wherein the plurality of sensors are disposed between the user and the plurality of compressible cells, and
wherein the plurality of measurements comprises at least one selected from a group consisting of a pressure measurement, a temperature measurement and a humidity measurement in the contact area.

15. The bed of claim 13, further comprising:
detecting a sustained duration of the pressure ulcer risk index exceeding the pre-determined threshold; and
generating, in response to the detecting, an alert to a care taker of the user.

16. The bed of claim 11, wherein inflating the plurality of compressible cells based on the plurality of measurements comprises:
computing, based on the plurality of measurements, an indication of the user leaving the mattress;
selecting, in response to the indication of the user leaving the mattress, a target compressible cell from the plurality of compressible cells based on a pre-determined criterion for retaining the user on the mattress; and
adjusting the air supplied to the target compressible cell to facilitate retaining the user on the mattress.

17. The bed of claim 16, further comprising:
detecting a sustained duration of the indication of the user leaving the mattress; and
generating, in response to the detecting, an alert to a care taker of the user.

18. The bed of claim 11, wherein inflating the plurality of compressible cells based on the plurality of measurements comprises:
detecting, based on the plurality of measurements, an indication of the user changing posture;
selecting, in response to the indication of the user changing posture, a target compressible cell from the plurality of compressible cells based on a pre-determined criterion for assisting the user changing posture; and
adjusting the air supplied to the target compressible cell to assist the user changing posture.

19. The bed of claim 11, wherein inflating the plurality of compressible cells based on the plurality of measurements comprises:
detecting, based on the plurality of measurements, a bottom out condition of a target compressible cell of the plurality of compressible cells; and
adjusting the air supplied to the target compressible cell to alleviate the bottom out condition.

20. The bed of claim 11,
wherein the plurality of compressible cells are coupled to form a compressible cell sheet,
wherein the plurality of sensors are coupled to form a sensor sheet, and
wherein the sensor sheet is coupled to the compressible cell sheet to maintain a corresponding relationship between the plurality of compressible cells and the plurality of sensors.

21. The bed of claim 20,
wherein the sensor sheet is integrated in a bedding item separate from and coupled to the compressible cell sheet.

22. A method for patient care, comprising:
inflating, by a pressure control device, a plurality of compressible cells each contacting a user in a contact area of a plurality of contact areas of the user;
generating, by a plurality of sensors corresponding to the plurality of compressible cells, a plurality of measurements;
selecting, by the pressure control device and based on the plurality of measurements, a target compressible cell from the plurality of compressible cells; and
adjusting, by the pressure control device and in response to the selecting, an inflation state of the selected target compressible cell,
wherein each of the plurality of measurements relates to the contact area of a corresponding compressible cell,
wherein the plurality of sensors are coupled to form a sensor sheet,
wherein the plurality of compressible cells are coupled to form a compressible cell sheet, and wherein the sensor sheet is attached to the compressible cell sheet to maintain a corresponding relationship between the plurality of compressible cells and the plurality of sensors.

23. The method of claim 22, wherein the pressure control device supplies air to inflate the plurality of compressible cells based on the plurality of measurements and releases the air to adjust an inflation level of the plurality of compressible cells based on the plurality of measurements.

24. The method of claim 22, wherein inflating the plurality of compressible cells based on the plurality of measurements comprises:
   computing, based on the plurality of measurements, a pressure ulcer risk index;
   iteratively selecting, in response to the pressure ulcer risk index exceeding a pre-determined threshold, a target compressible cell from the plurality of compressible cells based on a pre-determined criterion for reducing the pressure ulcer risk index; and
   iteratively adjusting, in response to the pressure ulcer risk index exceeding the pre-determined threshold, the air supplied to the target compressible cell to alleviate a pressure ulcer risk,
   wherein said each of the plurality of measurements comprises a contact pressure measurement in the contact area.

25. The method of claim 24,
   wherein the plurality of sensors are disposed between the user and the plurality of compressible cells, and
   wherein the plurality of measurements comprises at least one selected from a group consisting of a pressure measurement, a temperature measurement and a humidity measurement of the contact area.

26. The method of claim 24, further comprising:
   detecting a sustained duration of the pressure ulcer risk index exceeding the pre-determined threshold; and
   generating, in response to the detecting, an alert to a care taker of the user.

27. The method of claim 26, further comprising:
   detecting a sustained duration of the indication of the user leaving the mattress; and
   generating, in response to the detecting, an alert to a care taker of the user.

28. The method of claim 22, wherein inflating the plurality of compressible cells based on the plurality of measurements comprises:
   computing, based on the plurality of measurements, an indication of the user leaving the mattress;
   selecting, in response to the indication of the user leaving the mattress, a target compressible cell from the plurality of compressible cells based on a pre-determined criterion for retaining the user on the mattress; and
   adjusting the air supplied to the target compressible cell to facilitate retaining the user on the mattress.

29. The method of claim 22, wherein inflating the plurality of compressible cells based on the plurality of measurements comprises:
   detecting, based on the plurality of measurements, an indication of the user changing posture;
   selecting, in response to the indication of the user changing posture, a target compressible cell from the plurality of compressible cells based on a pre-determined criterion for assisting the user changing posture; and
   adjusting the air supplied to the target compressible cell to assist the user changing posture.

30. The method of claim 22, wherein inflating the plurality of compressible cells based on the plurality of measurements comprises:
   detecting, based on the plurality of measurements, a bottom out condition of a target compressible cell of the plurality of compressible cells; and
   adjusting the air supplied to the target compressible cell to alleviate the bottom out condition.

\* \* \* \* \*